(12) United States Patent
Sauer et al.

(10) Patent No.: US 11,357,499 B2
(45) Date of Patent: Jun. 14, 2022

(54) APPARATUS FOR MITRAL VALVE REPAIR AND METHODS THEREOF

(71) Applicant: LSI Solutions, Inc., Victor, NY (US)

(72) Inventors: Jude S. Sauer, Pittsford, NY (US); Angelo John Martellaro, Victor, NY (US)

(73) Assignee: LSI Solutions, Inc., Victor, NY (US)

( * ) Notice: Subject to any disclaimer, the term of this patent is extended or adjusted under 35 U.S.C. 154(b) by 386 days.

(21) Appl. No.: 15/240,334

(22) Filed: Aug. 18, 2016

(65) Prior Publication Data

US 2017/0049435 A1 Feb. 23, 2017

Related U.S. Application Data

(60) Provisional application No. 62/206,499, filed on Aug. 18, 2015.

(51) Int. Cl.
*A61F 2/24* (2006.01)
*A61B 17/04* (2006.01)
*A61B 17/00* (2006.01)

(52) U.S. Cl.
CPC ...... *A61B 17/0487* (2013.01); *A61B 17/0469* (2013.01); *A61B 17/0485* (2013.01);
(Continued)

(58) Field of Classification Search
CPC ............ A61B 17/0401; A61B 17/0485; A61B 17/0487; A61B 2017/0404;
(Continued)

(56) References Cited

U.S. PATENT DOCUMENTS 5,431,666 A * 7/1995 Sauer ................. A61B 17/0469
606/139
5,520,702 A * 5/1996 Sauer ................. A61B 17/0469
29/751
(Continued)

FOREIGN PATENT DOCUMENTS

EP 1716814 11/2006
GB 378288 8/1932
(Continued)

OTHER PUBLICATIONS

Jan. 5, 2018; International Search Report from PCT Application PCT/US2017/047582.
(Continued)

*Primary Examiner* — Erich G Herbermann
(74) *Attorney, Agent, or Firm* — Michael E. Coyne; Christopher B. Miller

(57) ABSTRACT

A surgical snare assembly is disclosed. The surgical snare assembly has a suture fastener having an entrance and an exit. The surgical snare assembly also has first and second suture engaging loops. The surgical snare assembly further has first and second handles configured such that: a) movement of the first handle a first distance away from the suture fastener causes the first suture engaging loop to move through the suture fastener from the exit to the entrance; and b) movement of the second handle a second distance away from the suture fastener causes the second suture engaging loop to move through the suture fastener from the entrance to the exit.

5 Claims, 22 Drawing Sheets

(52) U.S. Cl.
CPC .. *A61F 2/2457* (2013.01); *A61B 2017/00783* (2013.01); *A61B 2017/0454* (2013.01); *A61B 2017/0488* (2013.01)

(58) Field of Classification Search
CPC .... A61B 2017/0409; A61B 2017/0414; A61B 2017/042; A61B 2017/0454; A61B 2017/0464; A61B 2017/0488; A61B 2017/049; A61B 2017/0496; A61B 17/0491; A61F 2/2457; A61F 2/2454
See application file for complete search history.

(56) References Cited

U.S. PATENT DOCUMENTS

| | | |
|---|---|---|
| 6,533,796 B1 | 3/2003 | Sauer |
| 8,043,368 B2 | 10/2011 | Crabtree |
| 8,790,394 B2 | 7/2014 | Miller |
| 8,795,295 B2 | 8/2014 | Sauer |
| 9,204,965 B2 | 12/2015 | Longoria |
| 9,248,018 B2 | 2/2016 | Chawla |
| 2006/0229623 A1 | 10/2006 | Bonutti et al. |
| 2008/0249545 A1 | 10/2008 | Shikhman |
| 2009/0318961 A1 | 12/2009 | Stone et al. |
| 2012/0283749 A1* | 11/2012 | Sauer ............... A61B 17/0401 606/144 |
| 2013/0310874 A1 | 11/2013 | Torrie et al. |
| 2014/0276979 A1 | 9/2014 | Sauer |
| 2015/0142021 A1 | 5/2015 | Smith et al. |
| 2015/0289868 A1 | 10/2015 | Sauer |

FOREIGN PATENT DOCUMENTS

| | | |
|---|---|---|
| WO | 2013006820 | 1/2013 |
| WO | 2014028725 | 2/2014 |

OTHER PUBLICATIONS

Office Action for U.S. Appl. No. 15/240,334; Erich G. Herbermann; dated May 20, 2020.

* cited by examiner

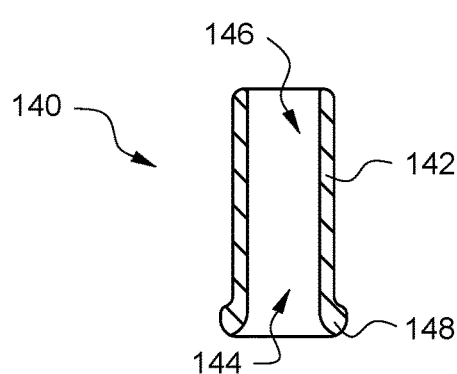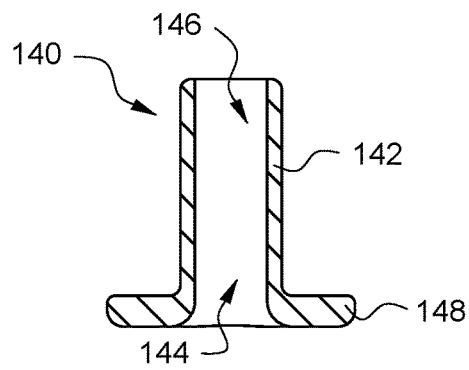
FIG. 11A    FIG. 11B
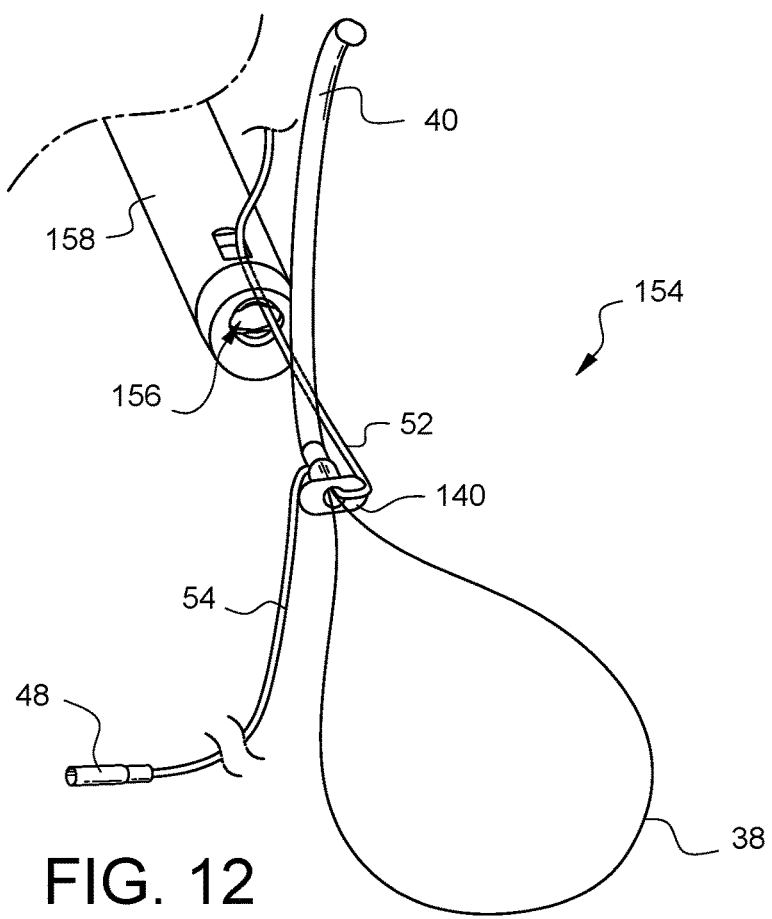
FIG. 12

APPARATUS FOR MITRAL VALVE REPAIR AND METHODS THEREOF

RELATED APPLICATION

This patent application claims priority to U.S. Provisional Patent Application No. 62/206,499 filed Aug. 18, 2015 and entitled "APPARATUS FOR MITRAL VALVE REPAIR AND METHODS THEREOF". The 62/206,499 application is hereby incorporated by reference in its entirety.

FIELD

The claimed invention relates to surgical suturing, and more specifically to minimally invasive surgical suturing devices for mitral valve repair and methods thereof.

BACKGROUND

The human heart relies on a series of one-way valves to help control the flow of blood through the chambers of the heart. For example, deoxygenated blood returns to the heart via the superior vena cava and the inferior vena cava, entering the right atrium. The heart muscle tissue contracts in a rhythmic, coordinated heartbeat, first with an atrial contraction which aids blood in the right atrium to pass through the tricuspid valve and into the right ventricle. Following atrial contraction, ventricular contraction occurs and the tricuspid valve closes. Ventricular contraction is stronger than atrial contraction, assisting blood flow through the pulmonic valve, out of the heart via the pulmonary artery, and to the lungs for oxygenation. Following the ventricular contraction, the pulmonic valve closes, preventing the backwards flow of blood from the pulmonary artery into the heart.

Oxygenated blood returns to the heart via the pulmonary veins, entering the left atrium. Left atrial contraction assists blood in the left atrium to pass through the mitral valve and into the left ventricle. Following the atrial contraction, ensuing ventricular contraction causes mitral valve closure, and pushes oxygenated blood from the left ventricle through the aortic valve and into the aorta where it then circulates throughout the body. Under nominal conditions, prolapse of the mitral valve is prevented during ventricular contraction by chordae attached between the mitral valve leaflets and papillary muscles. Following left ventricular contraction, the aortic valve closes, preventing the backwards flow of blood from the aorta into the heart.

Unfortunately, one or more of a person's heart valves can have or develop problems which adversely affect their function and, consequently, negatively impact the person's health. Generally, problems with heart valves can be organized into two categories: regurgitation and/or stenosis. Regurgitation occurs if a heart valve does not seal tightly, thereby allowing blood to flow back into a chamber rather than advancing through and out of the heart. This can cause the heart to work harder to remain an effective pump. Regurgitation is frequently observed when the mitral valve fails to close properly during a ventricular contraction. Mitral regurgitation can be caused by chordae stretching, tearing, or rupturing, along with other structural changes within the heart.

Neochordal replacement for stretched or torn chordae is one option to reduce regurgitation. In such a procedure, chords to be replaced are identified and dissected as required. A papillary suture is placed in a papillary muscle corresponding to the dissected chord. The papillary suture may optionally be pledgeted on one or both sides of the papillary muscle. A leaflet suture is also placed in the corresponding mitral valve leaflet. The papillary suture and the leaflet suture may then be tied or otherwise fastened together to create a replacement chord to help support the mitral valve leaflet and prevent regurgitation.

New minimally invasive surgical tools are becoming available which greatly facilitate placement of a single suture in both the papillary muscle and a corresponding mitral valve leaflet. While this creates a potentially simplified replacement structure for a chordae tendinae, there is still a desire to reliably secure the ends of the single suture as simply as possible in order to minimize the physiological footprint of the replacement structure. Hand-tied knots are difficult to form in a minimally invasive surgical setting. Mechanical knots are very reliable, but there is room for improvement in how such knots are applied.

Therefore, there is a need for efficient and reliable devices and methods for minimally invasive mitral valve repair.

SUMMARY

A surgical snare assembly is disclosed. The surgical snare assembly has a suture fastener having an entrance and an exit. The surgical snare assembly also has first and second suture engaging loops. The surgical snare assembly further has first and second handles configured such that: a) movement of the first handle a first distance away from the suture fastener causes the first suture engaging loop to move through the suture fastener from the exit to the entrance; and b) movement of the second handle a second distance away from the suture fastener causes the second suture engaging loop to move through the suture fastener from the entrance to the exit.

Another surgical snare assembly is disclosed. The surgical snare assembly has a suture fastener having an entrance and an exit. The surgical snare assembly also has a suture passed through the suture fastener with an entrance suture portion coming out of the entrance of the suture fastener and an exit suture portion coming out of the exit of the suture fastener, the suture having a ferrule coupled to the exit suture portion. The surgical snare assembly further has a suture engaging loop. The surgical snare assembly also has a handle coupled to the suture engaging loop such that movement of the handle a first distance away from the suture fastener causes the suture engaging loop to move through the suture fastener from the entrance to the exit.

A suture fastener applicator is disclosed. The suture fastener applicator has a suture fastener receiver and a snare outlet. The suture fastener applicator also has a surgical snare assembly. The surgical snare assembly has a suture fastener having an entrance and an exit. The surgical snare assembly also has a suture passed through the suture fastener with an entrance suture portion coming out of the entrance of the suture fastener and an exit suture portion coming out of the exit of the suture fastener, the suture having a ferrule coupled to the exit suture portion. The surgical snare assembly further has a suture engaging loop. The surgical snare assembly also has a handle coupled to the suture engaging loop such that movement of the handle a first distance away from the suture fastener causes the suture engaging loop to move through the suture fastener from the entrance to the exit. The exit of the suture fastener is inserted into the suture fastener receiver, while the entrance faces outward. The entrance suture portion and the handle protrude out of the snare outlet. The exit suture portion protrudes out of the suture fastener receiver.

A suture fastener is also disclosed. The suture fastener has a crimpable sleeve having an entrance and an exit. The suture fastener also has a base adjacent the entrance of the crimpable sleeve, wherein the base, when viewed from an entrance elevation, is longer in a first direction than in a second direction substantially perpendicular to the first direction.

BRIEF DESCRIPTION OF THE DRAWINGS

FIG. 1F-1 is an enlarged view of FIG. 1F.

FIGS. 11A and 11B are side and front cross-sectional views, respectively, of the suture fastener embodiment of FIG. 9.

FIG. 12 illustrates one embodiment of a surgical snare assembly having a suture fastener like the suture fastener embodied in FIG. 9.

Figure 1A:
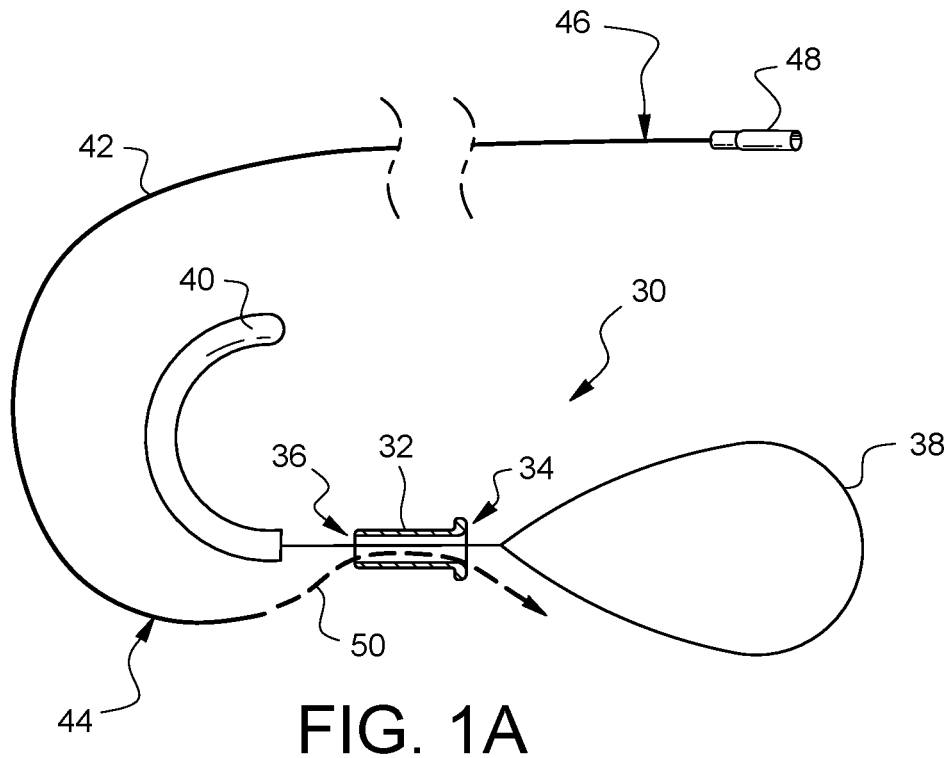
FIG. 1A is a partial cross-sectional view illustrating one embodiment of a surgical snare assembly prior to being fully assembled.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A illustrates a surgical snare assembly 30 prior to being fully assembled. The surgical snare assembly 30 has a suture fastener 32 with an entrance 34 and an exit 36. The suture fastener 32 is illustrated in a cross-sectional view to better illustrate the channel passing therethrough from the entrance 34 to the exit 36. The assembly 30 also has a suture engaging loop 38 coupled to a handle 40. In this embodiment, the handle 40 is positioned on the exit 36 side of the fastener 32, while the suture engaging loop 38 is positioned on the entrance 34 side of the fastener 32. Movement of the handle 40 a first distance away from the suture fastener 32 will cause the suture engaging loop to be pulled through the suture fastener 32 from the entrance 34 to the exit 36. A suture 42 having a first end 44 and a second end 46 is also present. A ferrule 48 is coupled to the second end 46 of the suture 42. The ferrule 48 is configured to be able to engage a suturing needle (none shown) such that the needle can pull the ferrule 48 (and its corresponding suture) through tissue which the needle has pierced.

Figure 1B:
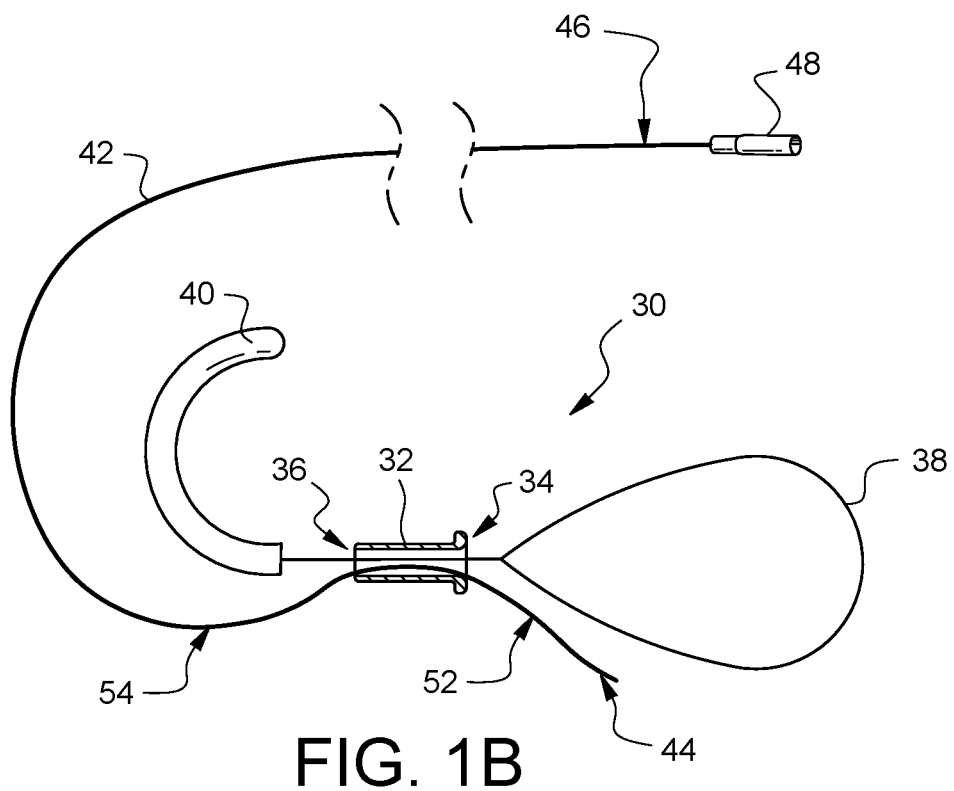
FIG. 1B is a partial cross-sectional view of one embodiment of a fully assembled surgical snare assembly.

In FIG. 1A, the first end 44 of the suture 42 has not been passed through the suture fastener 32 yet, although an intended path 50 for the suture end 44 is illustrated. FIG. 1B illustrates the fully assembled surgical snare assembly 30 with the first suture end 44 passed through the suture fastener 32. An entrance suture portion 52 protrudes out of the entrance 34 of the suture fastener 32, while an exit suture portion 54 protrudes out of the exit 36 of the suture fastener 32. The ferrule 48 is coupled to the exit suture portion 54.

Figure 1C:
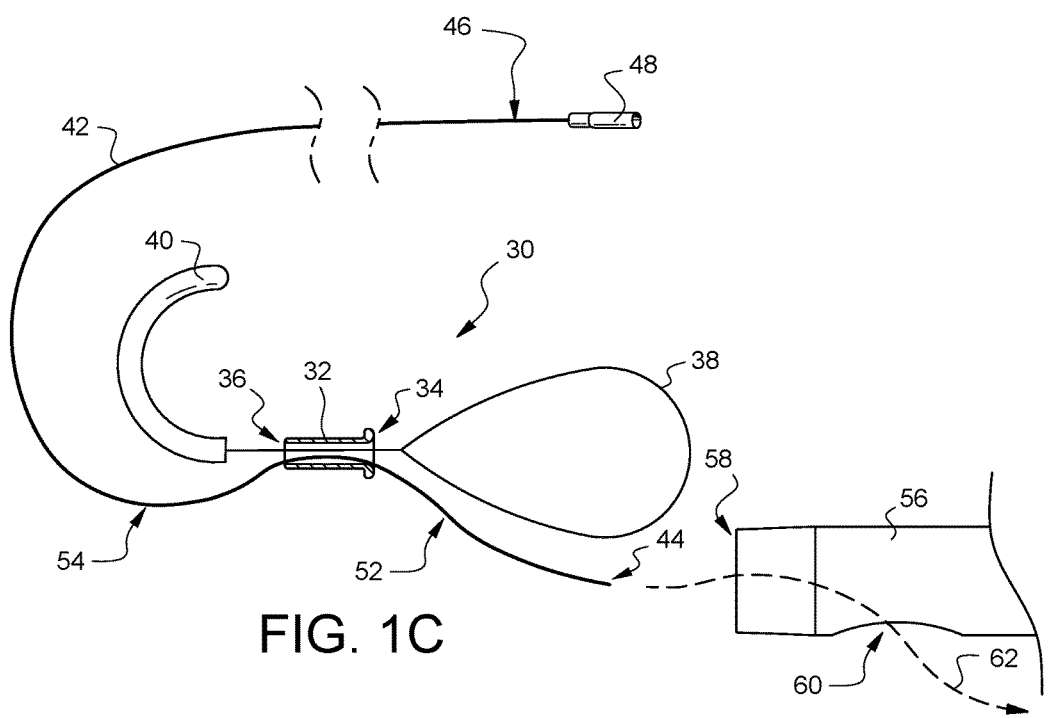
In FIG. 1C, a distal end of a suture fastener applicator is introduced with the surgical snare assembly of FIG. 1B.
Figure 1D:
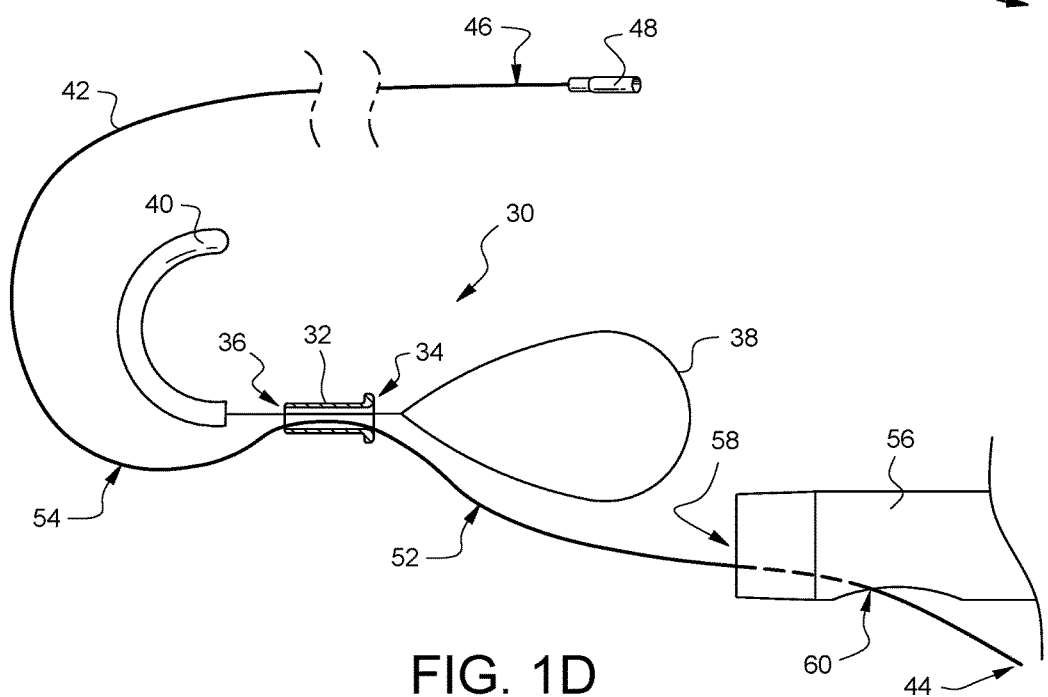
FIGS. 1D-1F illustrate how the surgical snare assembly of FIG. 1B may be loaded into the suture fastener applicator of FIG. 1C to form a suture fastener applicator assembly.

In FIG. 1C, a distal end of a suture fastener applicator 56 is introduced. The applicator 56 has a suture fastener receiver 58 and a snare outlet 60. Such suture fastener applicators 56 are known to those skilled in the art. As just one example, the COR-KNOT® device from LSI Solutions, Inc. of Victor, N.Y. (www.lsisolutions.com) is one such device. The entrance suture portion 52 of the surgical snare assembly 30 will be threaded on path 62 through the suture fastener receiver 58 and out of the snare outlet 60 as shown in FIG. 1D.

Figure 1E:
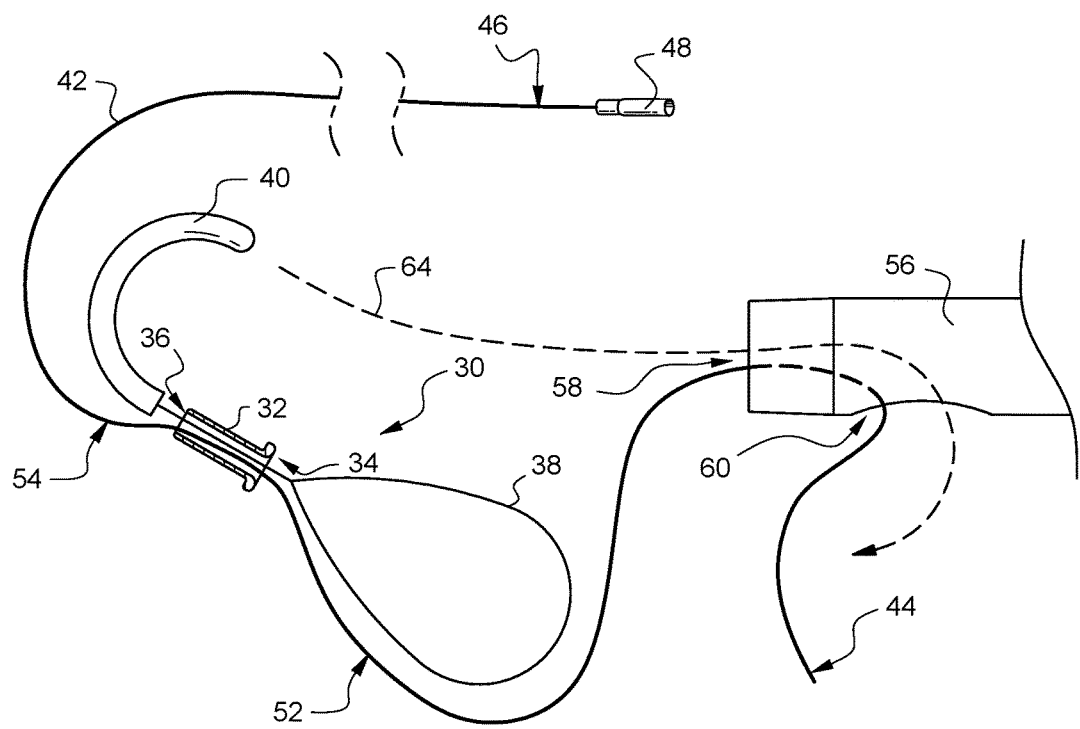

In FIG. 1E, the handle 40 is brought towards the suture fastener applicator 56. The handle 40 of the surgical snare assembly 30 will be passed on path 64 through the suture fastener receiver 58 and out of the snare outlet 60 as shown in FIG. 1F.

Figure 1F:
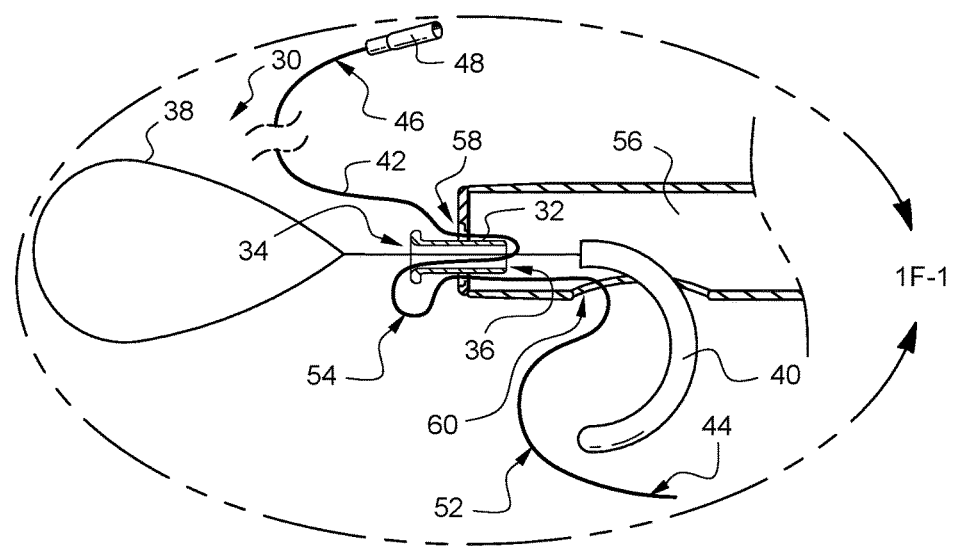
Figures 1, 1F:
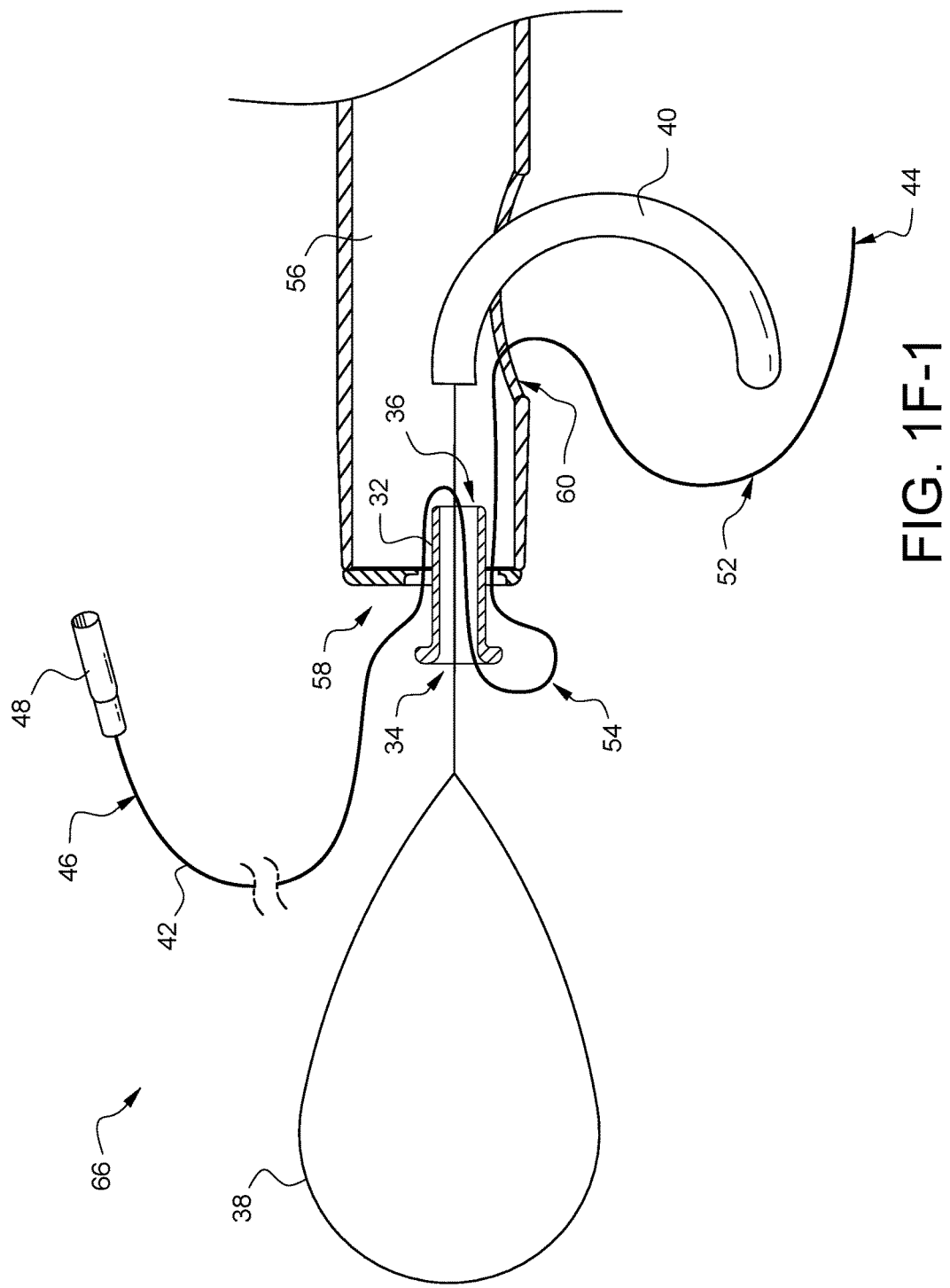

FIG. 1F-1 is an enlarged view of FIG. 1F. The exit 36 of the suture fastener 32 has been inserted into the suture fastener receiver 58, while the entrance 34 faces outward. For ease of explanation, the suture fastener 32 is only shown partially inserted into the suture fastener receiver 58 so that the suture paths may be seen more clearly. In practice, however, the suture fastener 32 could be inserted more fully. Other illustrations also follow this convention. The entrance suture portion 52 and the handle 40 protrude out of the snare outlet 60. The exit suture portion 54 protrudes out of the suture fastener receiver 58. The assembly illustrated in FIG. 1F-1 may be referred to as a suture fastener applicator assembly 66.

Figure 1G:
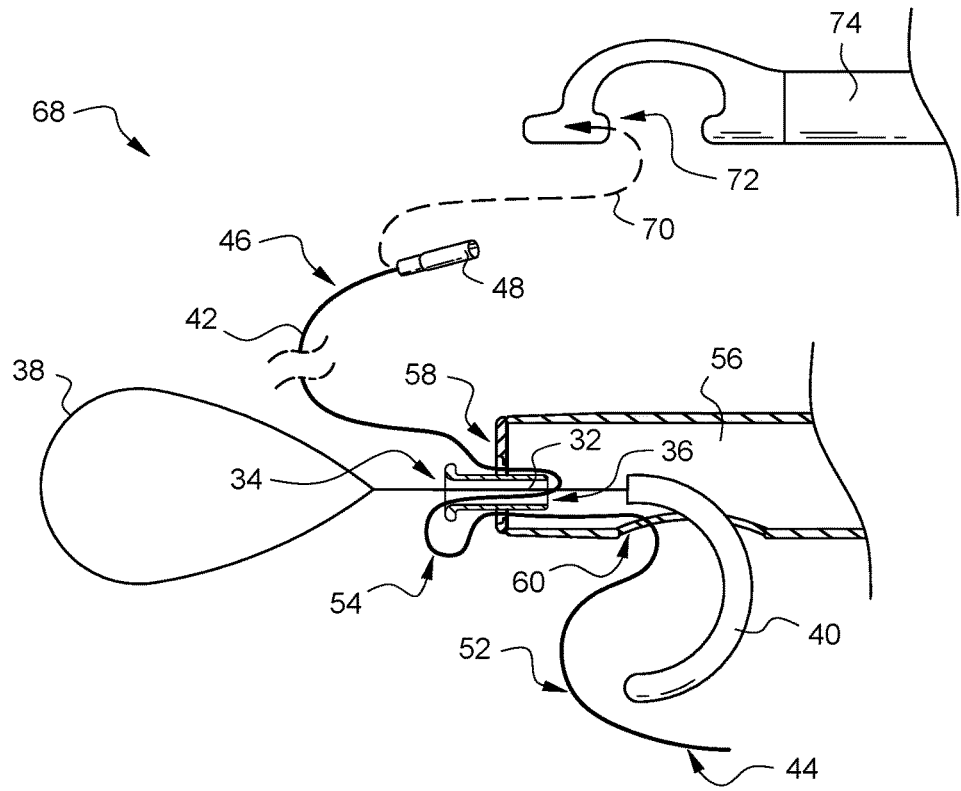
FIGS. 1G-1H illustrate one embodiment of a larger suturing assembly which may be formed by combining the suture fastener applicator assembly of FIG. 1F with a minimally invasive suturing device.
Figure 1H:
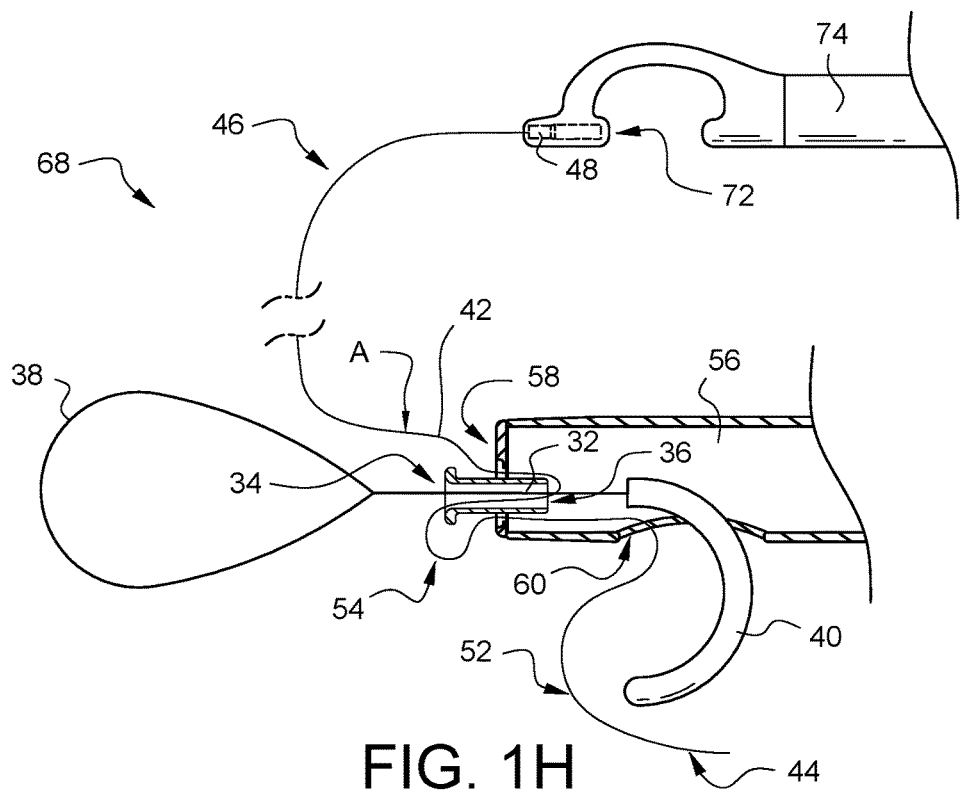

The suture fastener applicator assembly 66 may be part of a larger suturing assembly 68 illustrated in FIGS. 1G and 1H. The ferrule 48 may be passed on a path 70 such that it is installed in a ferrule receiver 72 of a minimally invasive suturing device 74. Minimally invasive suturing devices are known to those skilled in the art. One exemplary device is the RD180® from LSI Solutions, Inc. of Victor, N.Y. (www.lsisolutions.com)

Figure 2:
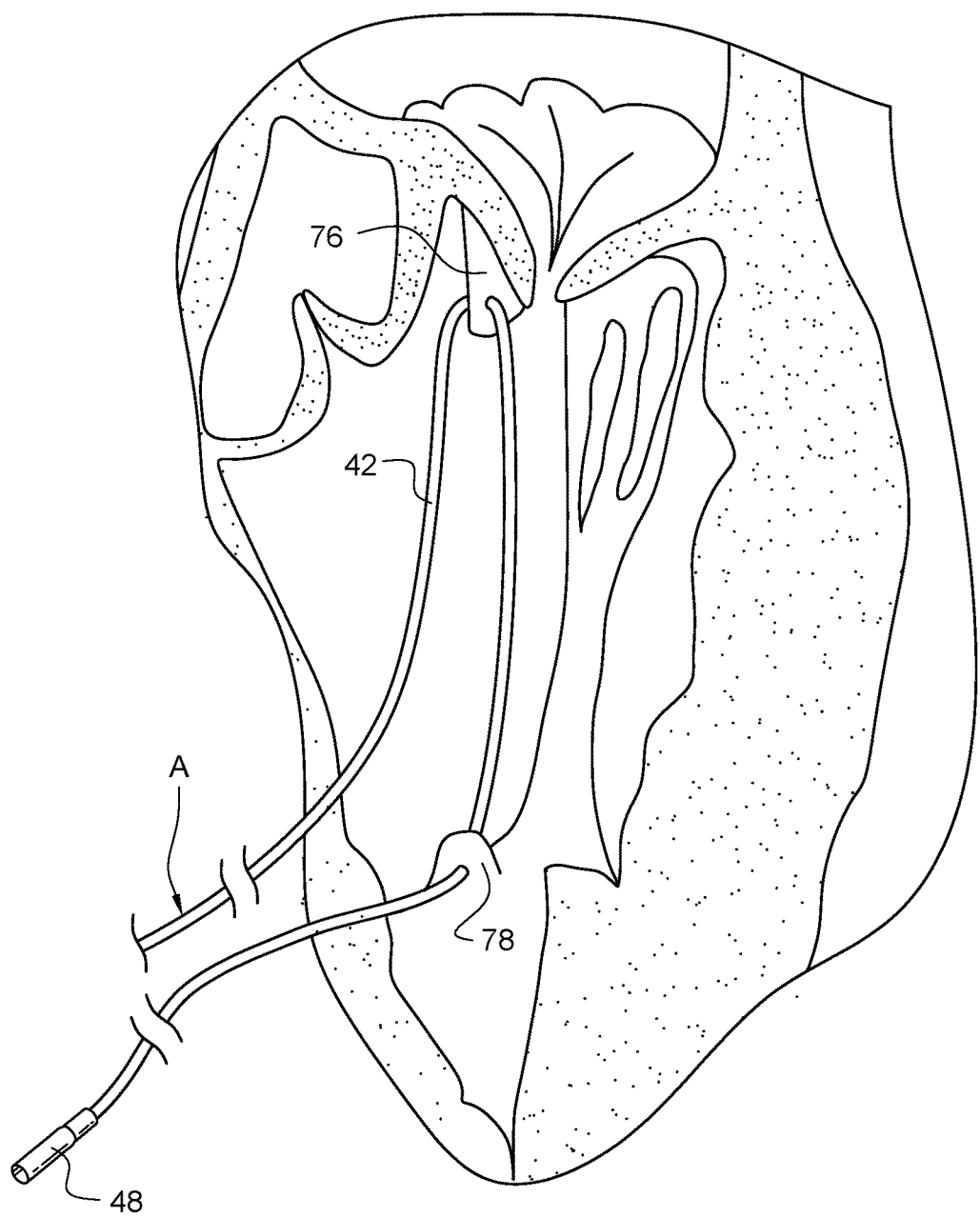
FIG. 2 illustrates a surgical situation where a suture has been placed through a mitral valve leaflet and then through a papillary muscle.
Figure 3A:
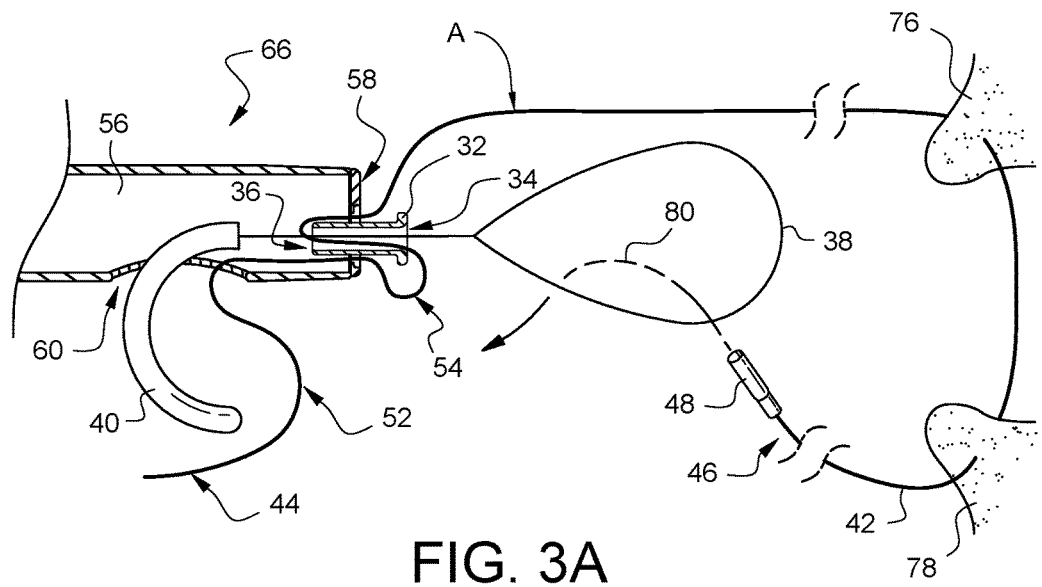
FIGS. 3A-3F illustrate one embodiment of a method by which the suture ends of FIG. 2 may be fastened together to form a replacement chord by using the suture fastener applicator assembly of FIG. 1F.
Figure 3B:
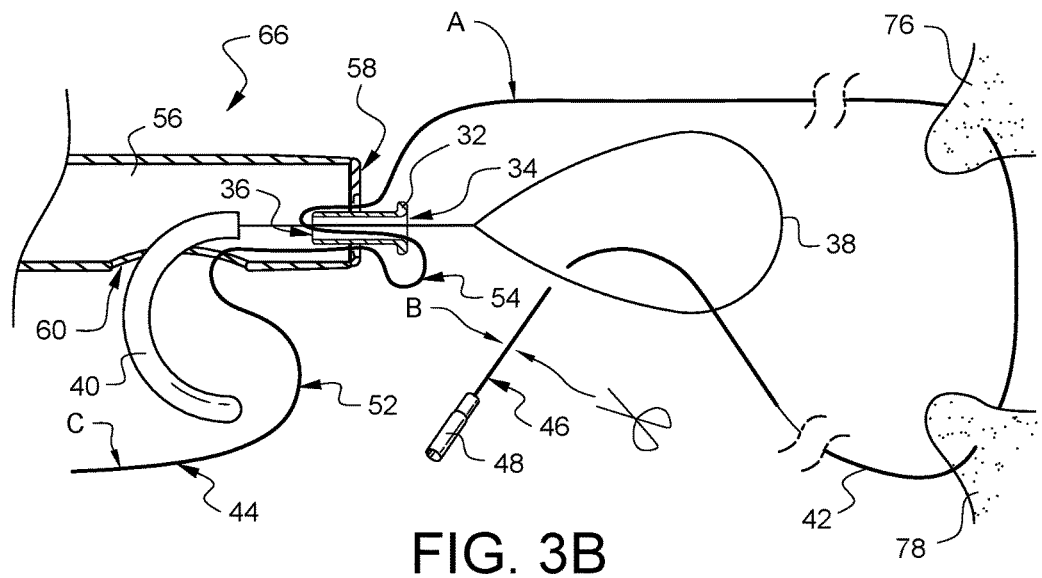

The suture 42 is long enough that the suturing device 74 may be used to place suture stitches in a patient at one or more desired locations. For example, a surgical situation is illustrated in FIG. 2. The suture 42 has been placed through a mitral valve leaflet 76 and then through a papillary muscle 78. The ferrule 48 has been released from the suturing device 74 (not shown) and the suture portion A (part of the exit suture portion 54) passes back to the suture fastener applicator assembly 66 of FIG. 1F-1 (not shown in this view). FIG. 3A schematically illustrates this surgical situation, including the suture fastener applicator assembly 66. The ferrule 48 can be passed along the path 80 through the suture engaging loop 38 as shown in FIG. 3B. Suture portions A and B are part of the exit suture portion 54, but suture portion A is between the tissue 76, 78 and the suture fastener applicator assembly 66, while suture portion B is between the second end 46 of suture 42 and the tissue 78, 76. The entrance suture portion 52 which exits the snare outlet 60 is labelled suture portion C.

Figure 3C:
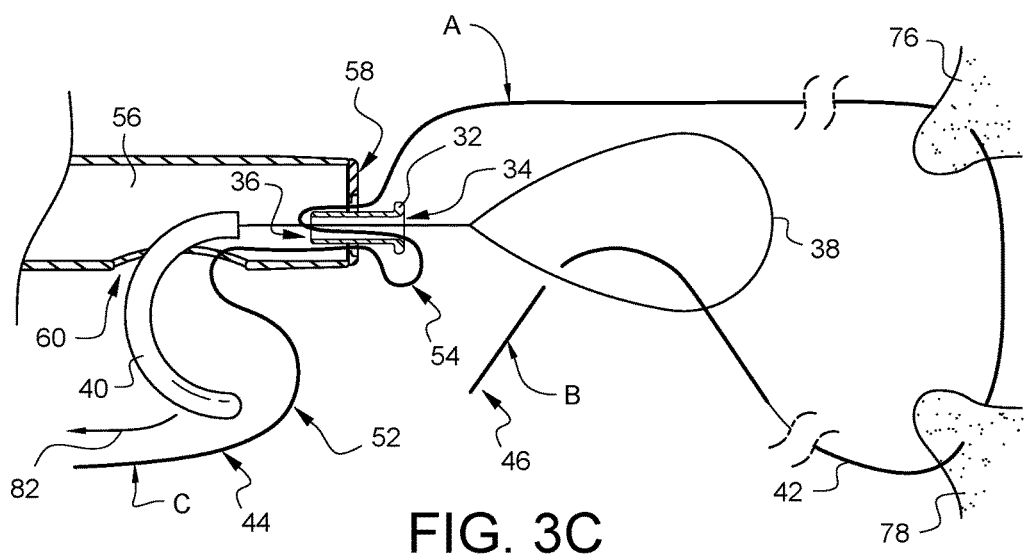
Figure 3D:
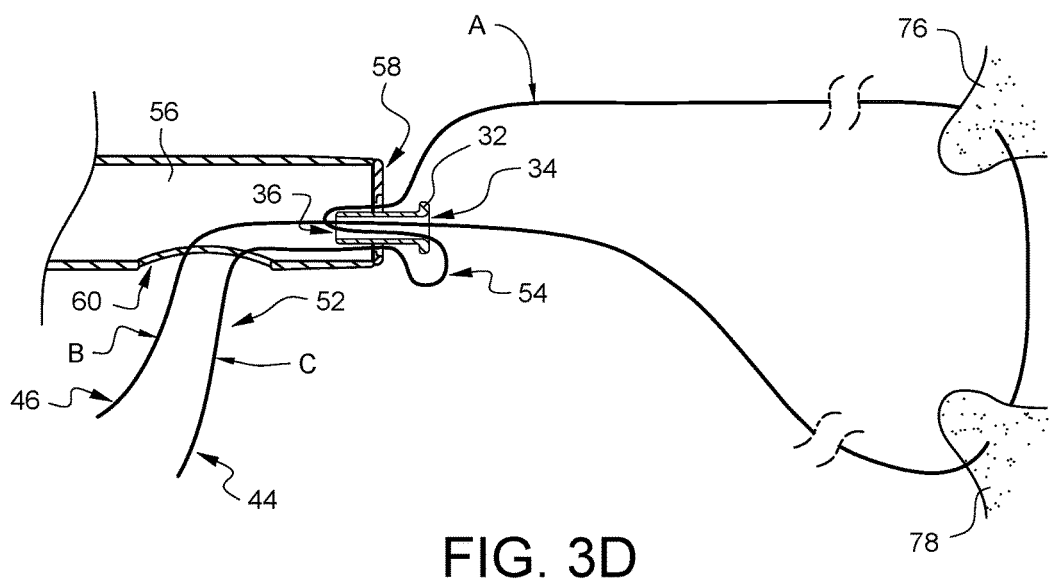

The ferrule 48 shown in FIG. 3B may be cut off the second suture end 46, resulting in the situation shown in FIG. 3C, where the suture portion B is still passed through the suture engaging loop 38. The handle 40 may be pulled in direction 82, causing the suture engaging loop 38 to pull the suture portion B through the entrance 34 of the suture fastener 32, out the exit 36 of the suture fastener 32, and out the snare outlet 60 as illustrated in FIG. 3D. The suture portions C and B (corresponding to the first and second suture ends 44, 46) are now together, protruding from the snare outlet 60.

Figure 3E:
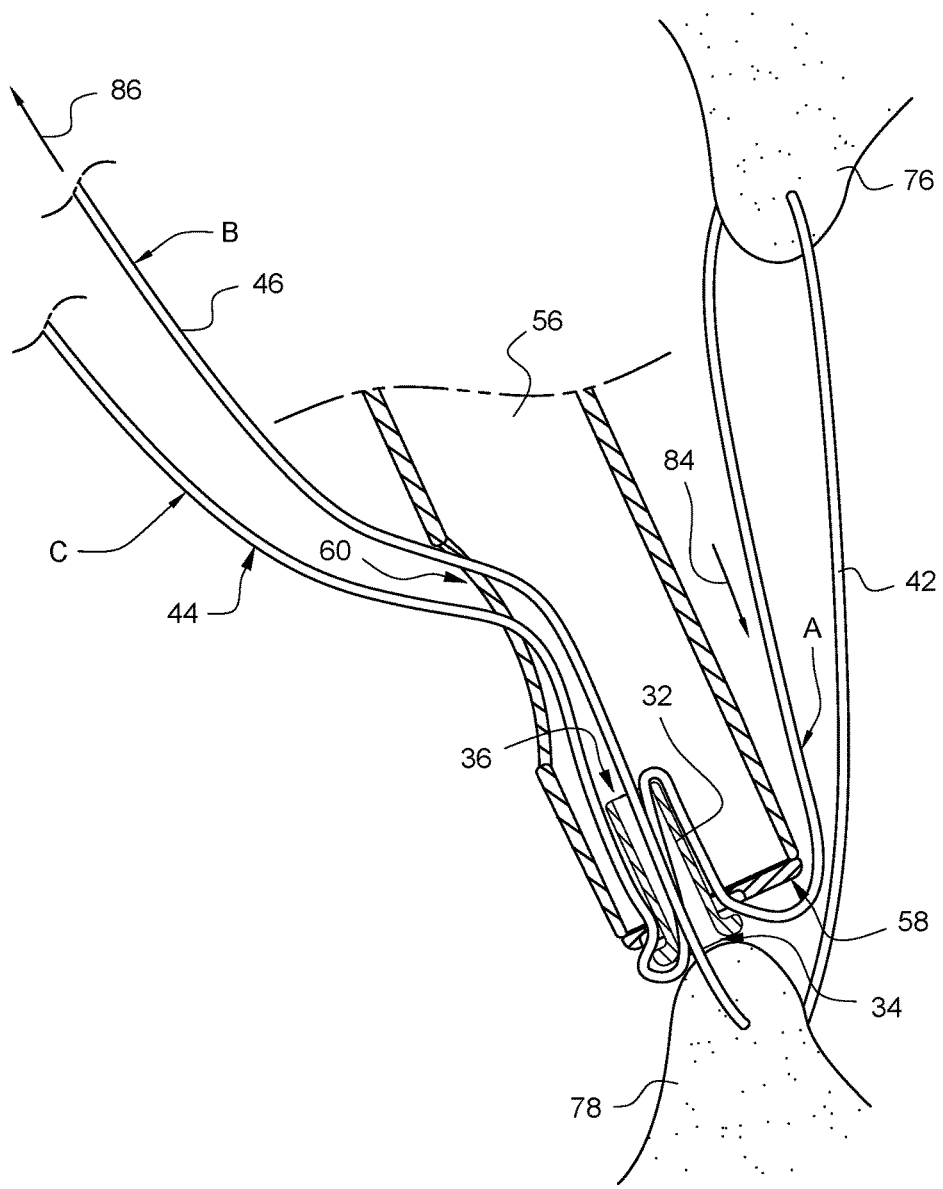
Figure 3F:
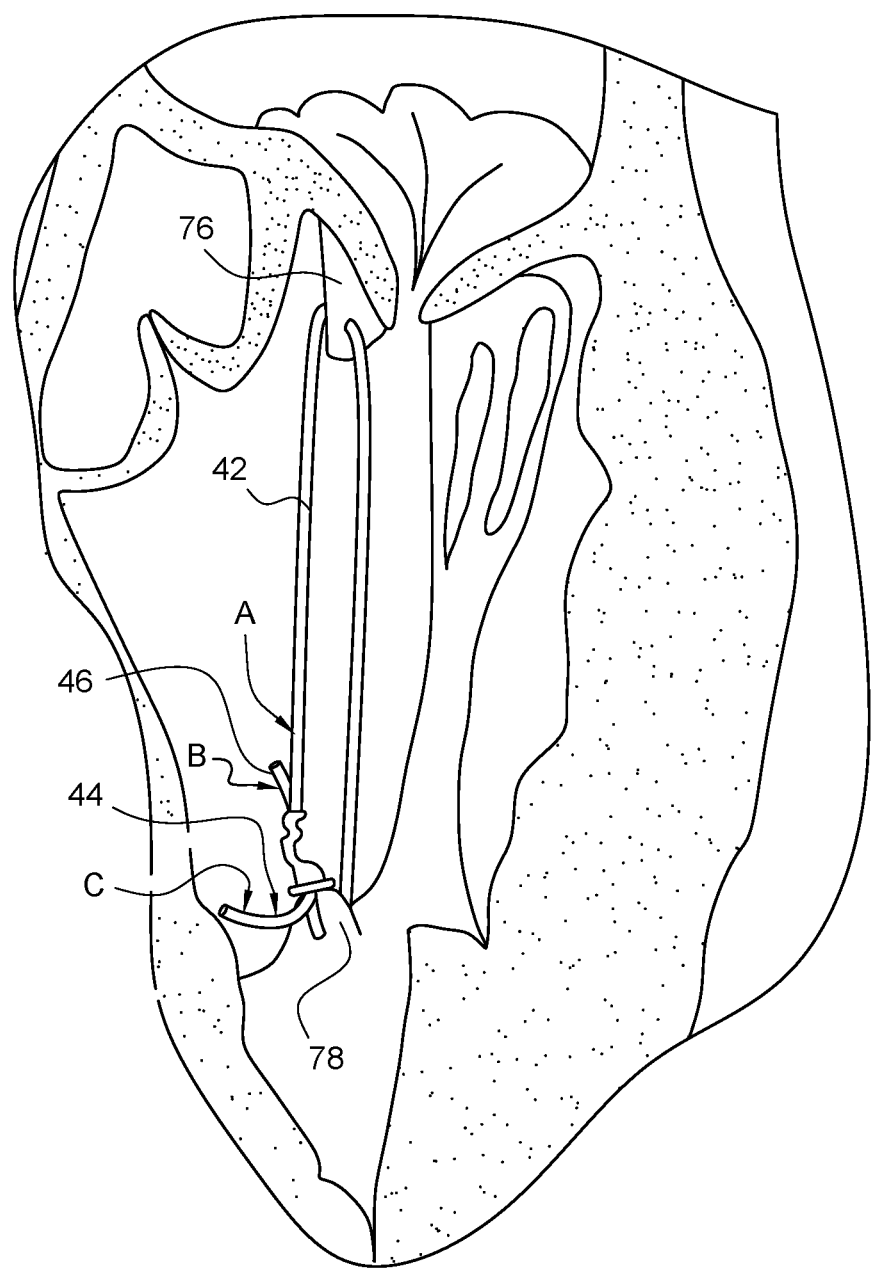

As shown in the enlarged view of FIG. 3E, the suture fastener applicator 56 is moved 84 so that the entrance 34 of the suture fastener 32 is placed against the papillary muscle 78, while the suture ends B and C are tensioned 86 individually and/or separately to achieve a desired suture length between the mitral leaflet 76 and the papillary muscle 78. Given the routing of the suture, it may be easiest to adjust suture end B. When the desired suture length is achieved, the suture fastener applicator 56 is activated, causing the suture fastener 32 to fasten onto the suture passing therethrough. In this example, the suture fastener applicator 56 crimps the suture fastener 32, the suture ends B and C can be trimmed, and the suture fastener applicator 56 can be removed, resulting in the secured suture 42 illustrated in FIG. 3F. This secured single suture acts as a replacement chordae tendinae as part of a mitral valve repair procedure.

FIGS. 4A, 5A, 6A, 7A, and 8 all illustrate different embodiments of a precursor surgical snare assembly 88, 90, 92, 94, 96, respectively, which can be advantageously used to produce a surgical snare assembly such as assembly 30 of FIG. 1B, or its equivalent. Each precursor surgical snare assembly includes a suture fastener 32 having an entrance 34 and an exit 36. The assembly 88 of FIG. 4A has first and second suture engaging loops 98, 100. A first handle 102 is coupled to the first suture engaging loop 98, while a second handle 104 is coupled to the second suture engaging loop 100. The handles 102, 104 are configured such that movement of the first handle 102 a first distance away from the suture fastener 32 causes the first suture engaging loop 98 to move through the suture fastener 32 from the exit 36 to the entrance 34. Furthermore, movement of the second handle 104 a second distance away from the suture fastener 32 causes the second suture engaging loop 100 to move through the suture fastener 32 from the entrance 34 to the exit 36. A suture end 44 may be inserted into the first suture engaging loop 98, and subsequently pulled through the suture fastener 32 from the exit 36 to the entrance 34 by pulling the first handle 102 as illustrated in FIG. 4B. The first suture loop 98 and its coupled first handle 102 may be set aside, and the remaining surgical snare assembly 30 is ready for use as discussed above.

Figure 5A:
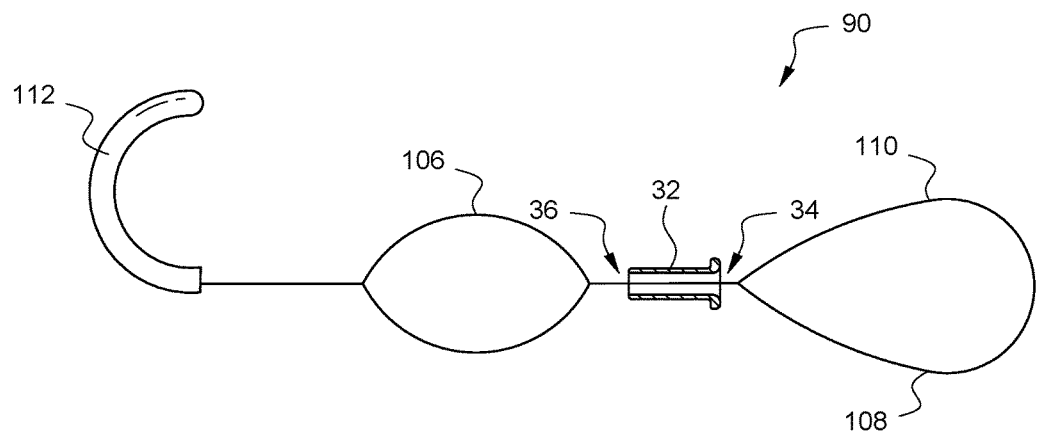
FIG. 5A illustrates another embodiment of a precursor surgical snare assembly which can advantageously be used to produce a surgical snare assembly, such as the surgical snare assembly embodiment illustrated in FIG. 5B.
Figure 5B:
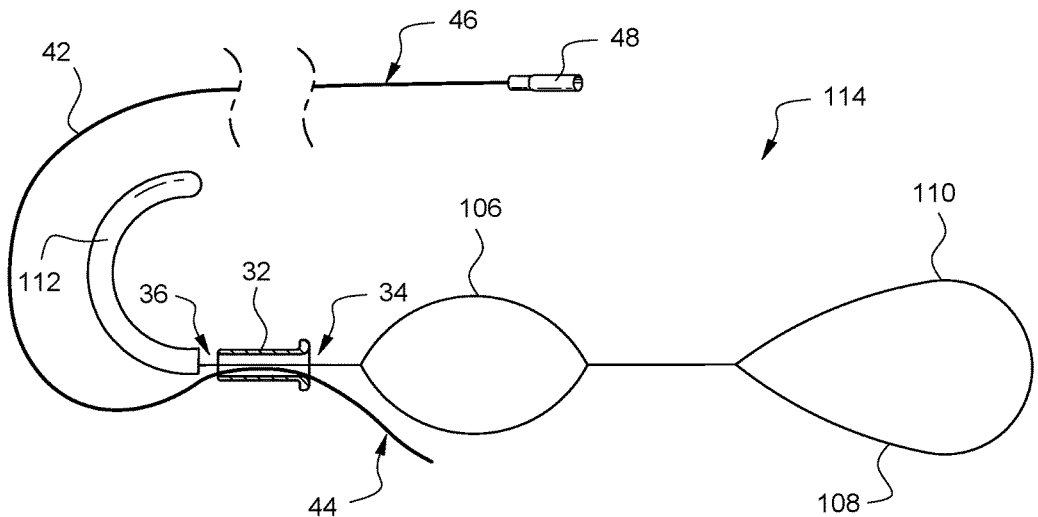

The assembly 90 of FIG. 5A has first and second suture engaging loops 106, 108. The second suture engaging loop 108 also acts as a first handle 110, and it is coupled to the first suture engaging loop 106. The assembly 90 also has a second handle 112 which is indirectly coupled to the second loop 108. The handles 110, 112 are configured such that movement of the first handle 110 a first distance away from the suture fastener 32 causes the first suture engaging loop 106 to move through the suture fastener 32 from the exit 36 to the entrance 34. Furthermore, movement of the second handle 112 a second distance away from the suture fastener 32 causes the second suture engaging loop 108 to move through the suture fastener 32 from the entrance 34 to the exit 36. A suture end 44 may be inserted into the first suture engaging loop 106, and subsequently pulled through the suture fastener 32 from the exit 36 to the entrance 34 by pulling the first handle 110 as illustrated in FIG. 5B. The remaining surgical snare assembly 114 is ready for use as discussed above, with either loop 106, 108 available for use as the suture engaging loop 38 from FIG. 1A.

Figure 6A:
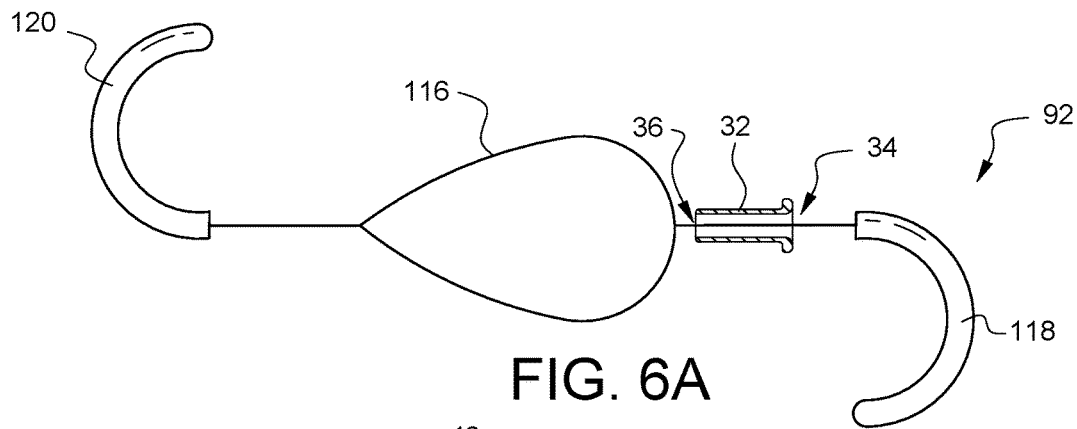
FIG. 6A illustrates a further embodiment of a precursor surgical snare assembly which can advantageously be used to produce a surgical snare assembly, such as the surgical snare assembly embodiment illustrated in FIG. 6C.
Figure 6B:
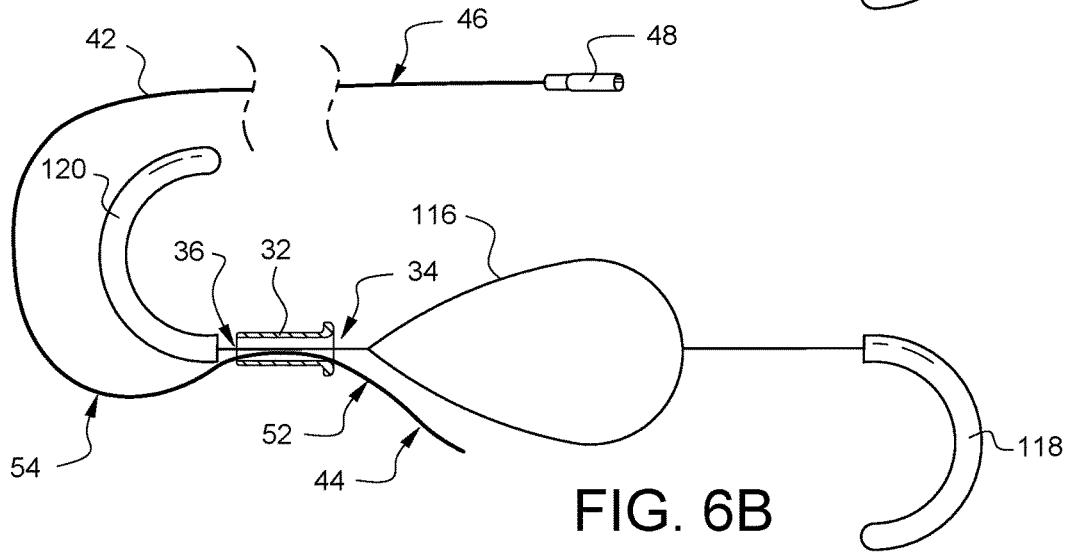
FIG. 6B illustrates an intermediate step in the production process between the precursor of FIG. 6A and the surgical snare assembly of FIG. 6C.
Figure 6C:
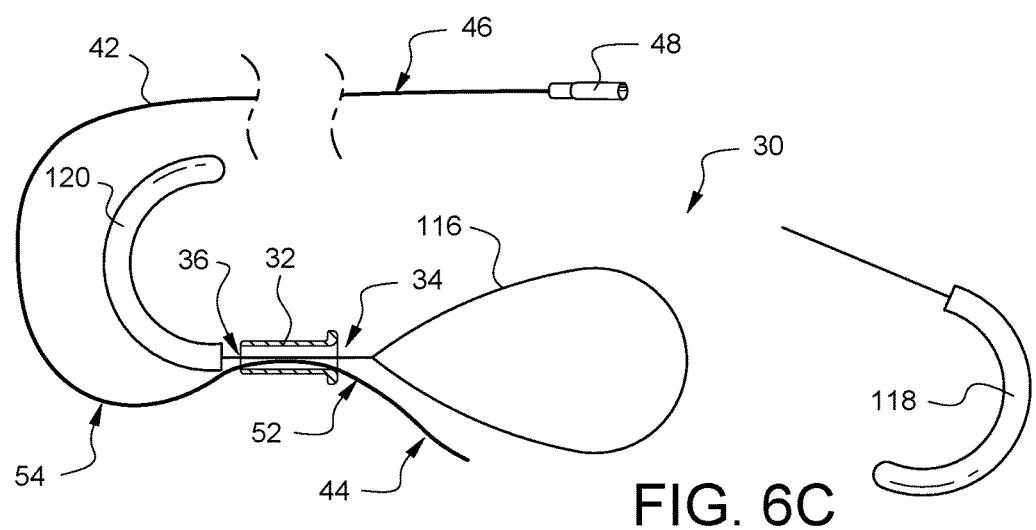

The assembly 92 of FIG. 6A has a suture engaging loop 116 which is both a first suture engaging loop and a second suture engaging loop. A first handle 118 is coupled to the suture engaging loop 116 (which operates as a first suture engaging loop when it is on the exit side of the fastener), while a second handle 120 is coupled to the suture engaging loop 116 (which also operates as a second suture engaging loop when it is on the entrance side of the suture fastener). The handles 118, 120 are configured such that movement of the first handle 118 a first distance away from the suture fastener 32 causes the first suture engaging loop 116 to move through the suture fastener 32 from the exit 36 to the entrance 34. Furthermore, movement of the second handle 120 a second distance away from the suture fastener 32 causes the second suture engaging loop 116 to move through the suture fastener 32 from the entrance 34 to the exit 36. A suture end 44 may be inserted into the first suture engaging loop 116, and subsequently pulled through the suture fastener 32 from the exit 36 to the entrance 34 by pulling the first handle 118 as illustrated in FIG. 6B. The first suture handle 118 may be removed and set aside as shown in FIG. 6C, and the remaining surgical snare assembly 30 is ready for use as discussed above.

Figure 7A:
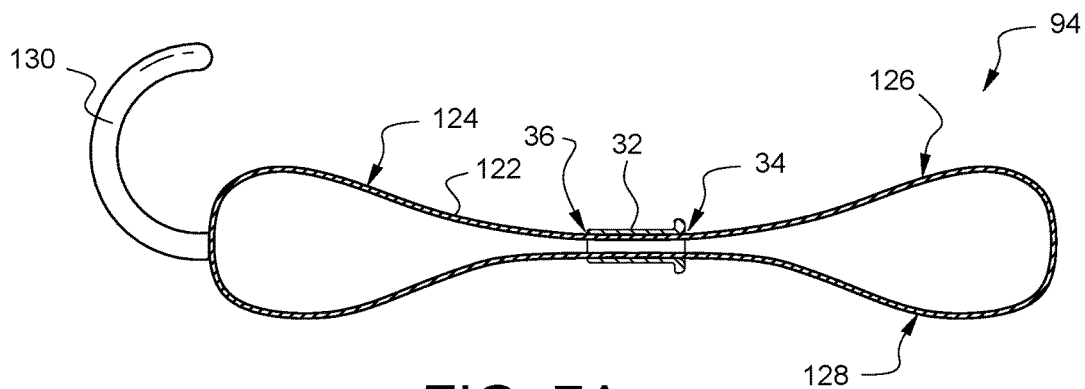
FIG. 7A illustrates another embodiment of a precursor surgical snare assembly which can advantageously be used to produce a surgical snare assembly, such as the surgical snare assembly embodiment illustrated in FIG. 7C.
Figure 7B:
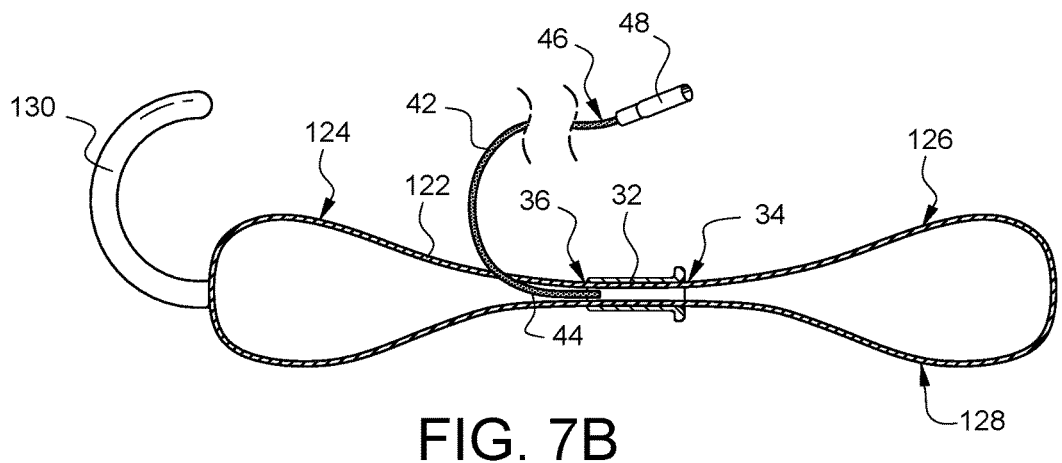
FIG. 7B illustrates an intermediate step in the production process between the precursor of FIG. 7A and the surgical snare assembly of FIG. 7C.
Figure 7C:
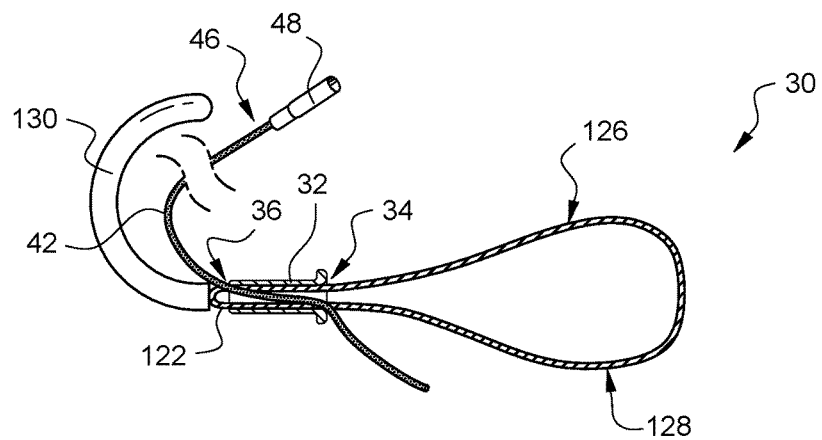

The assembly 94 of FIG. 7A has a suture engaging loop 122 which is both a first suture engaging loop 124 (on the exit side of the suture fastener) and a second suture engaging loop 126 (on the entrance side of the suture fastener). The second suture engaging loop 126 is also the first handle 128. The first handle 128 is coupled to the first suture engaging loop 124, while a second handle 130 is coupled to the second suture engaging loop 126. The handles 128, 130 are configured such that movement of the first handle 128 a first distance away from the suture fastener 32 causes the first suture engaging loop 124 to move through the suture fastener 32 from the exit 36 to the entrance 34. Furthermore, movement of the second handle 130 a second distance away from the suture fastener 32 causes the second suture engaging loop 126 to move through the suture fastener 32 from the entrance 34 to the exit 36. A suture end 44 may be pinched between the first suture engaging loop 124, and subsequently pulled through the suture fastener 32 from the exit 36 to the entrance 34 by pulling the first handle 128 as illustrated in FIG. 7B. The remaining surgical snare assembly 30 illustrated in FIG. 7C is ready for use as discussed above. It should be noted that the loop 122 is shown shortened for convenience in FIG. 7C, and is not drawn in corresponding scale with FIGS. 7A and 7B.

Figure 4A:
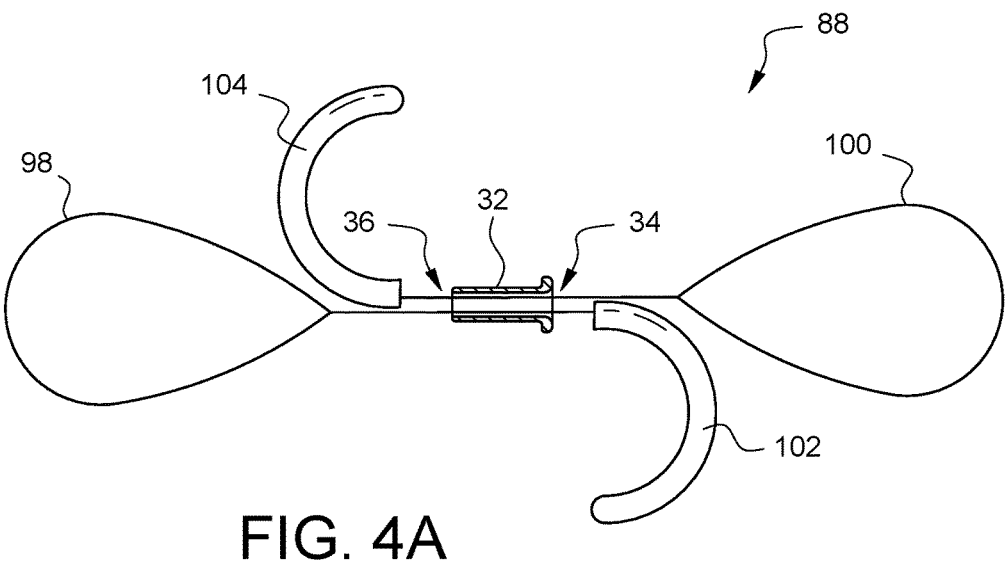
FIG. 4A illustrates one embodiment of a precursor surgical snare assembly which can advantageously be used to produce a surgical snare assembly, such as the surgical snare assembly embodiment illustrated in FIG. 4B.
Figure 4B:
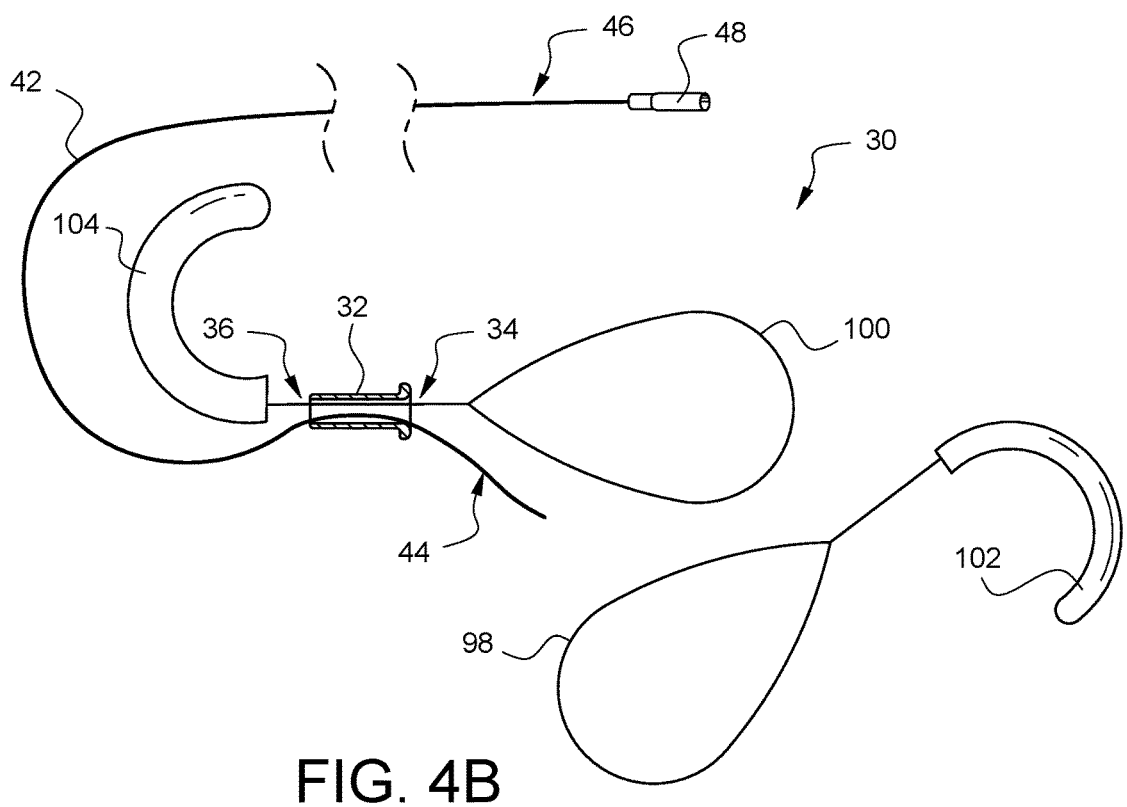
Figure 8:
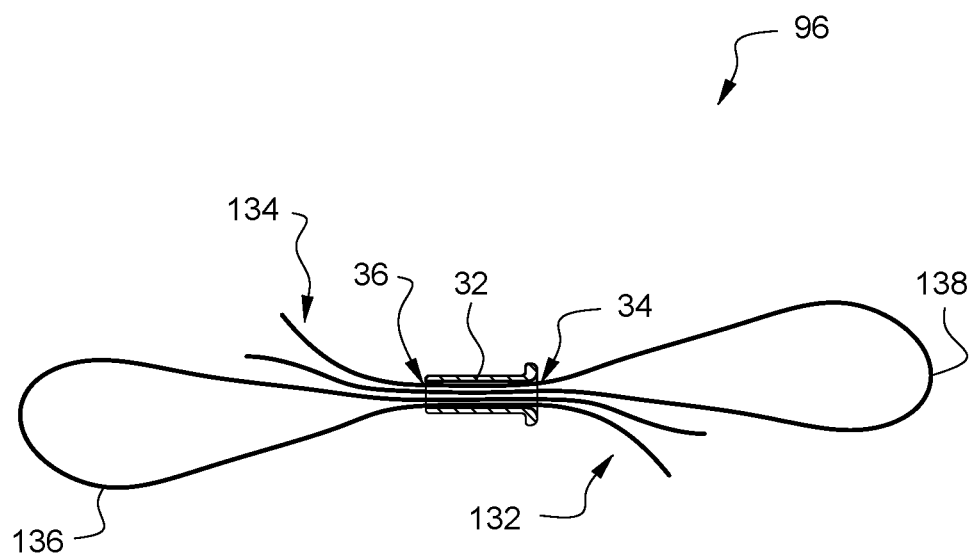
FIG. 8 illustrates a further embodiment of a precursor surgical snare assembly.

The precursor surgical snare assembly 96 of FIG. 8 shows an alternate embodiment of the FIG. 4A assembly where the first and second handles 132, 134 are made from loose ends of the first and second loops 136, 138. Operation of this precursor assembly 96 is otherwise like that of precursor assembly 88. Other embodiments are possible with a mix of handle types, and those skilled in the art will readily understand that many handle types may be used in light of the teaching of this specification.

Figure 9:
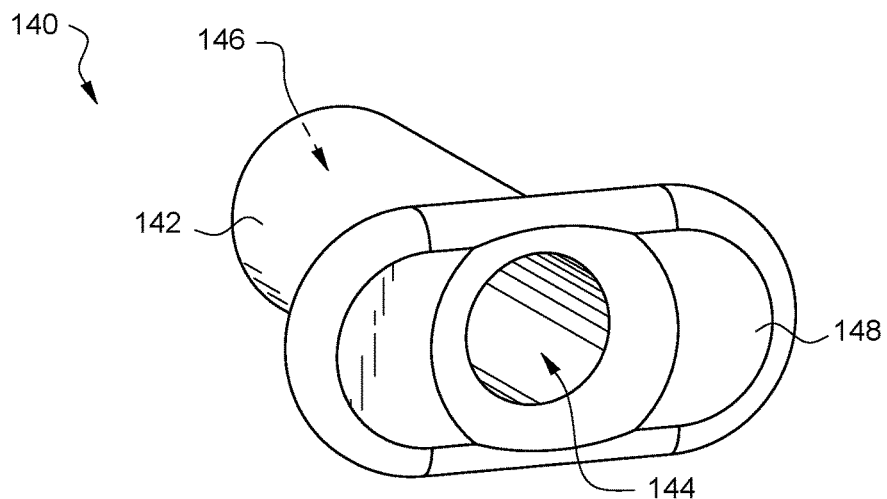
FIG. 9 is a perspective view illustrating one embodiment of an improved suture fastener.
Figure 10C:
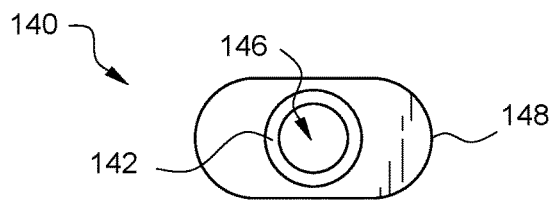
FIGS. 10A, 10B, 10C, and 10D illustrate front, right side, top, and bottom elevational views of the suture fastener embodiment of FIG. 9.
Figures 10A, 10B:
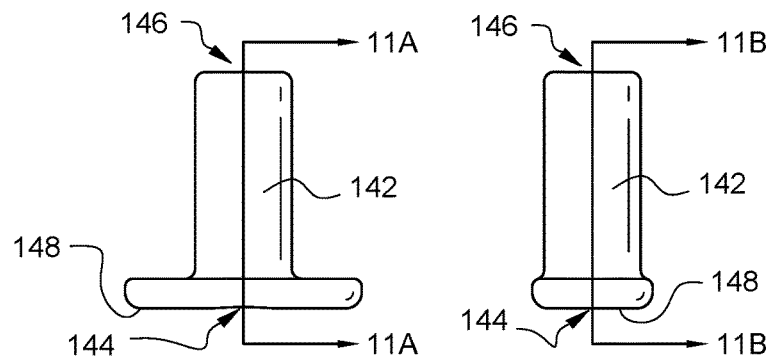
Figure 10D:
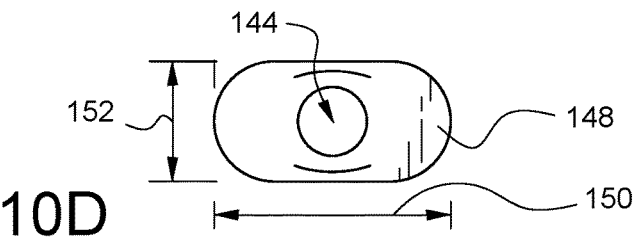

FIG. 9 illustrates one embodiment of an improved suture fastener 140 in a perspective view. FIGS. 10A, 10B, 10C, and 10D illustrate front, right side, top, and bottom elevational views of the suture fastener 140. The suture fastener 140 has a crimpable sleeve 142 having an entrance 144 and an exit 146. The improved suture fastener 140 also has a base 148 adjacent the entrance 144 of the crimpable sleeve 142. When viewed from an entrance elevation, such as from FIG. 10D, the base is longer in a first direction 150 than in a second direction 152 substantially perpendicular to the first direction 150. In some embodiments, the preferred ratio of the length of the base 148 in the first direction 150 to the length of the base 148 in the second direction 152 is approximately 2:1, although other embodiments may have smaller or greater ratios, provided the ratio is substantially greater than 1:1. FIG. 11A is a cross-sectional view of the suture fastener 140 of FIG. 10A, taken along cross-section line 11A-11A. FIG. 11B is a cross-sectional view of the suture fastener of FIG. 10B, taken along cross-section line 11B-11B.

As illustrated in FIG. 12, a suture fastener 140, such as the suture fastener of FIG. 9, may be used as part of a surgical snare assembly such as those discussed previously. It should be noted, however, that the surgical snare assemblies are not necessarily limited to having a suture fastener of a particular shape. If a suture fastener 140 such as the one shown in FIG. 12 is used, however, the suture fastener receiver 156 may be given a corresponding shape so that the orientation of the rounded rectangular base may be known relative to the applicator 158.

Figure 13:
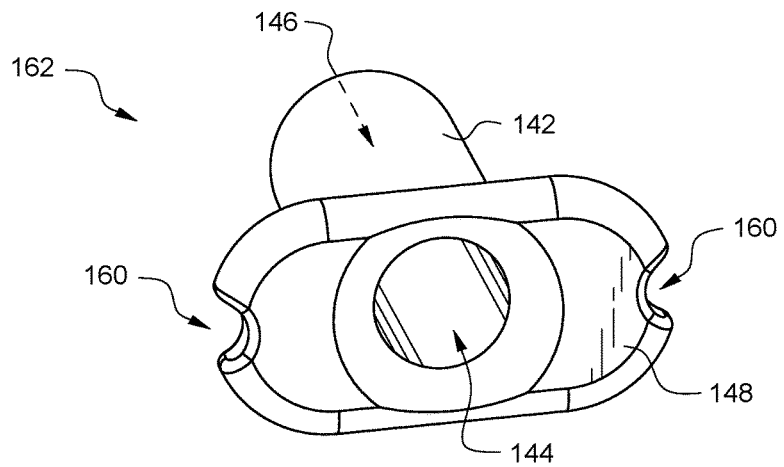
FIG. 13 is a perspective view illustrating another embodiment of an improved suture fastener, this embodiment being similar to the embodiment of FIG. 9, but also having one or more suture guides in the sides of the base of the suture fastener.

The exit suture portion 54 and the entrance suture portion 52 are routed past opposite sides of the base of suture fastener 140 in the example of FIG. 12. As illustrated in FIG. 13, it may be advantageous in some embodiments to provide one or more suture guides 160 in the sides of the base 148 of the suture fastener 162. The suture guides 160 can be used to help ensure the exit suture portion 54 and the entrance suture portion 52 are routed as desired relative to the base. This can help to ensure the exit and entrance suture portions 54, 52 do not interfere with the crimping action of the fastener applicator which holds the suture fastener.

Figure 14:
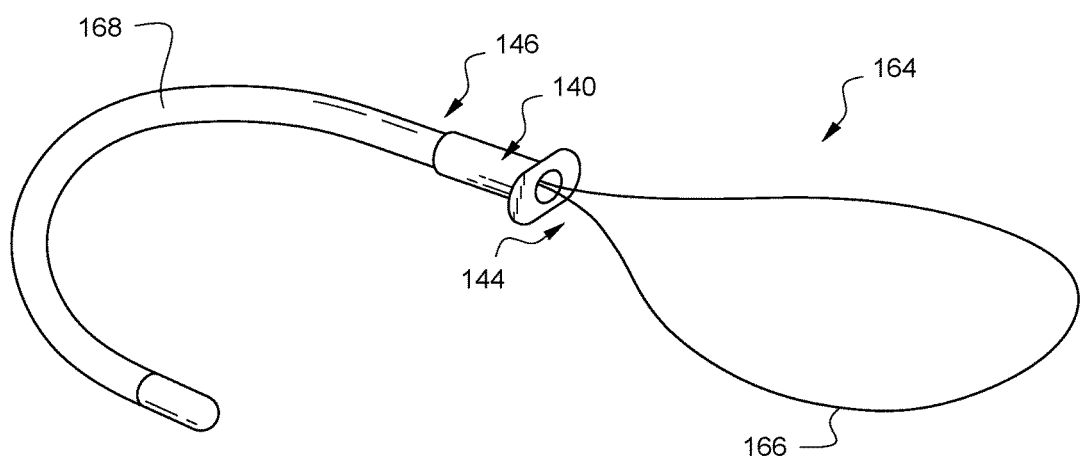
FIG. 14 illustrates another embodiment of a surgical snare assembly.

As illustrated in FIG. 14, a suture fastener 140 (the features of which have been discussed above) may be used as part of a surgical snare assembly 164 which has a suture engaging loop 166 passing through the entrance 144 of the fastener 140 and coupled to a handle 168 on the exit 146 side of the fastener. Such an assembly is useful for a variety of procedures, including a mitral valve repair procedure.

Figure 15:
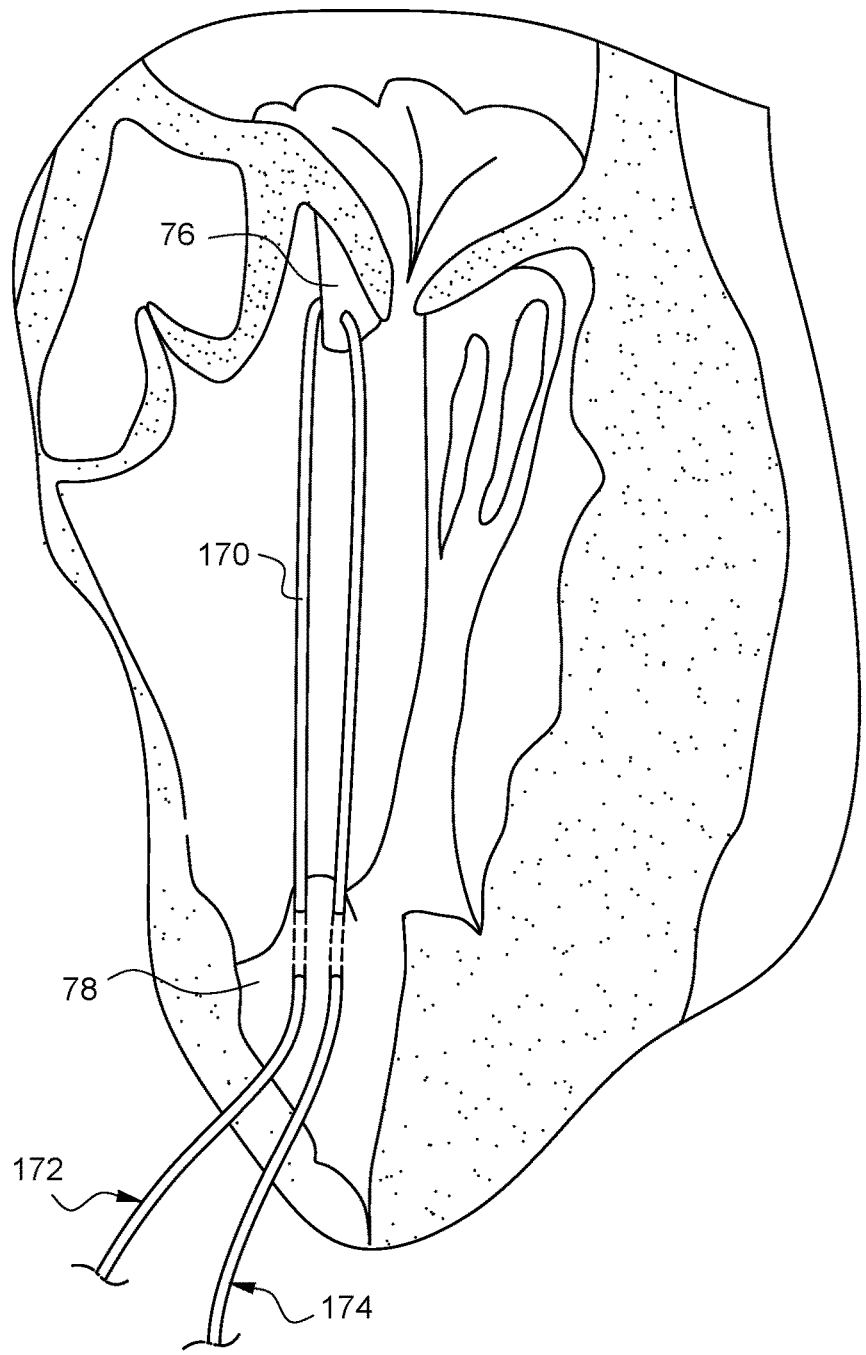
FIG. 15 presents a surgical situation in which a suture has been passed through a mitral valve leaflet, and then both ends of the suture have been passed down, through, and out of a papillary muscle.
Figure 16A:
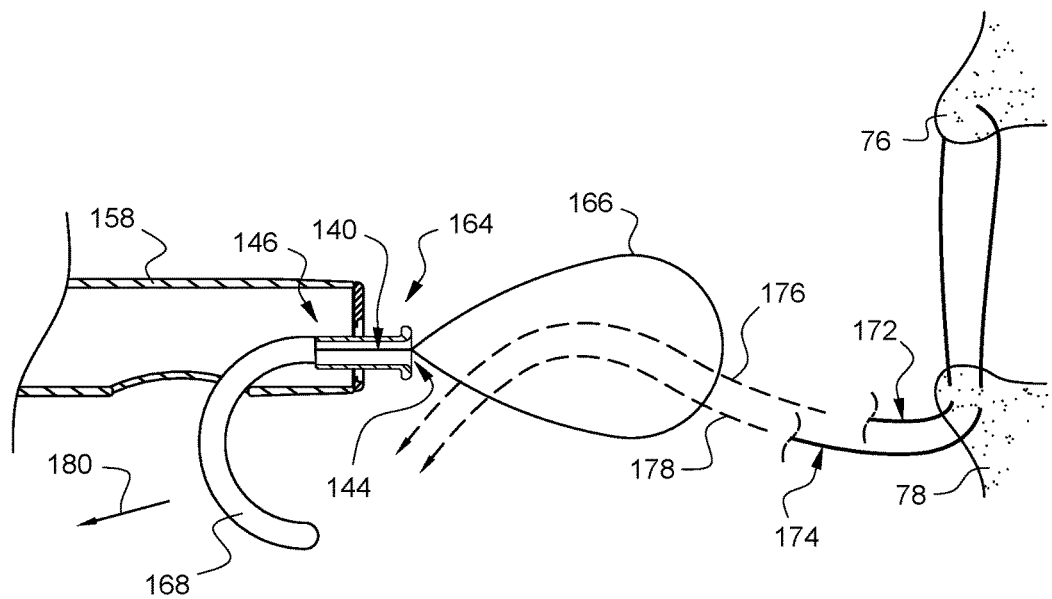
FIGS. 16A-16D illustrate one embodiment of a method whereby the suture snare assembly of FIG. 14 may be used in conjunction with a suture fastener applicator to apply the improved suture fastener embodiment of FIG. 9 to the suture ends exiting the papillary muscle in order to form a replacement chord for the mitral valve.
Figure 16B:
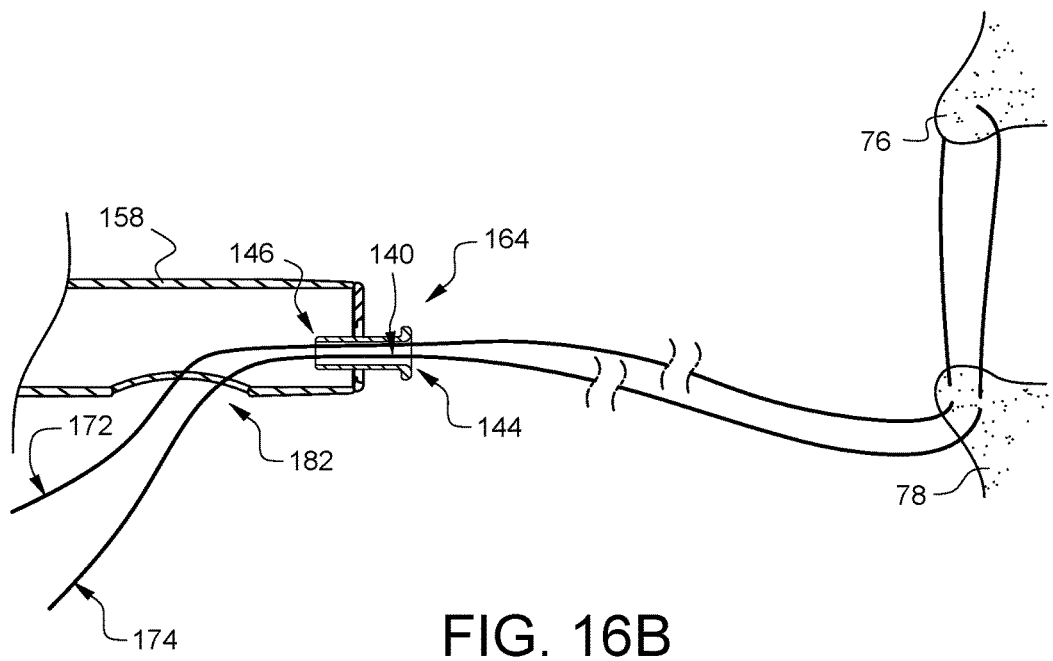

For example, consider the surgical situation presented in FIG. 15. A suture 170 has been passed through a mitral valve leaflet 76, and then both ends 172, 174 of the suture 170 have been passed down through and out of a papillary muscle 78. As illustrated in FIG. 16A, the snare assembly 164 of FIG. 14 may be installed in a suture fastener applicator as shown. The suture ends 172, 174 may be passed along paths 176, 178, through the suture engaging loop 166, and then the handle 168 may be pulled 180, resulting in the suture ends 172, 174 being drawn through the entrance 144 of the suture fastener 140, out the exit 146 of the suture fastener, and out of the snare outlet 182 of the applicator 158 as shown in FIG. 16B.

Figure 16C:
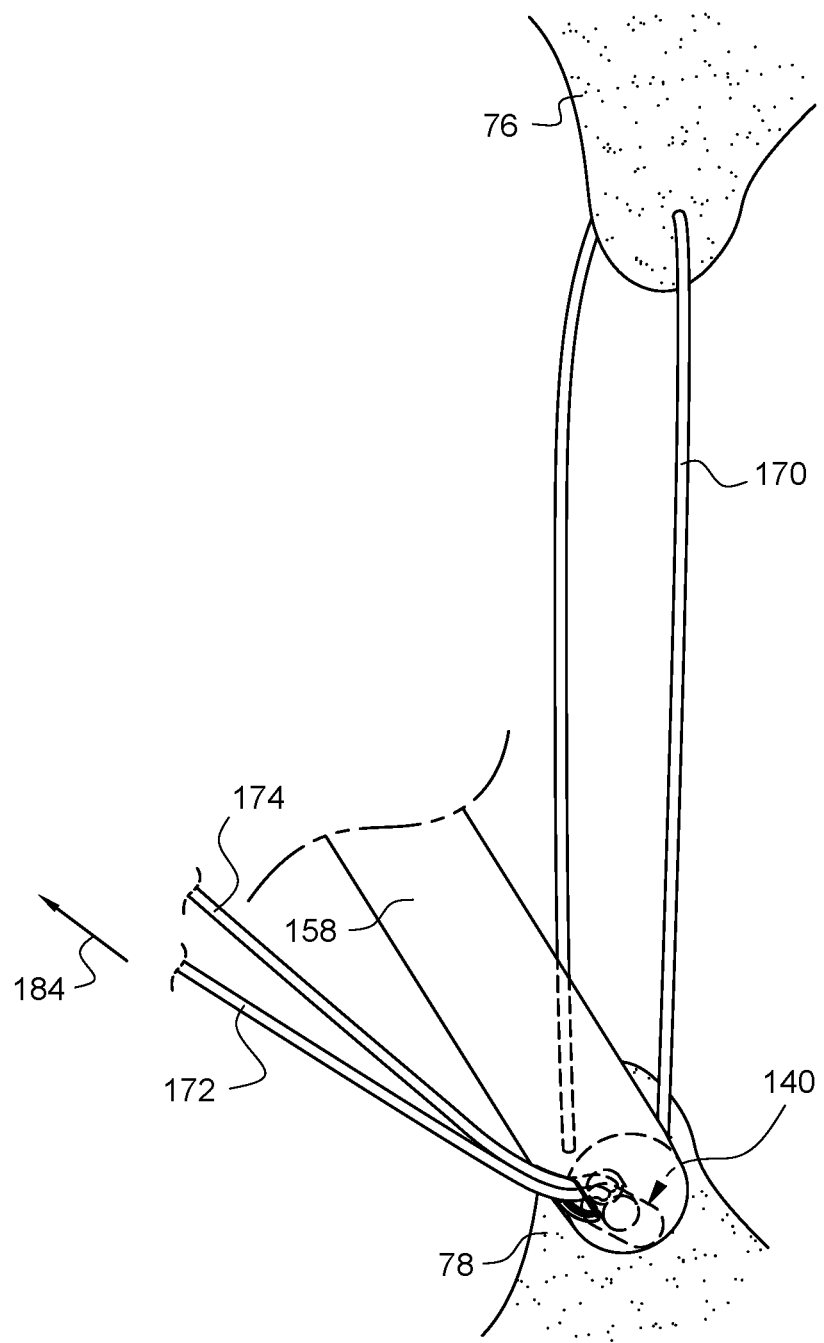
Figure 16D:
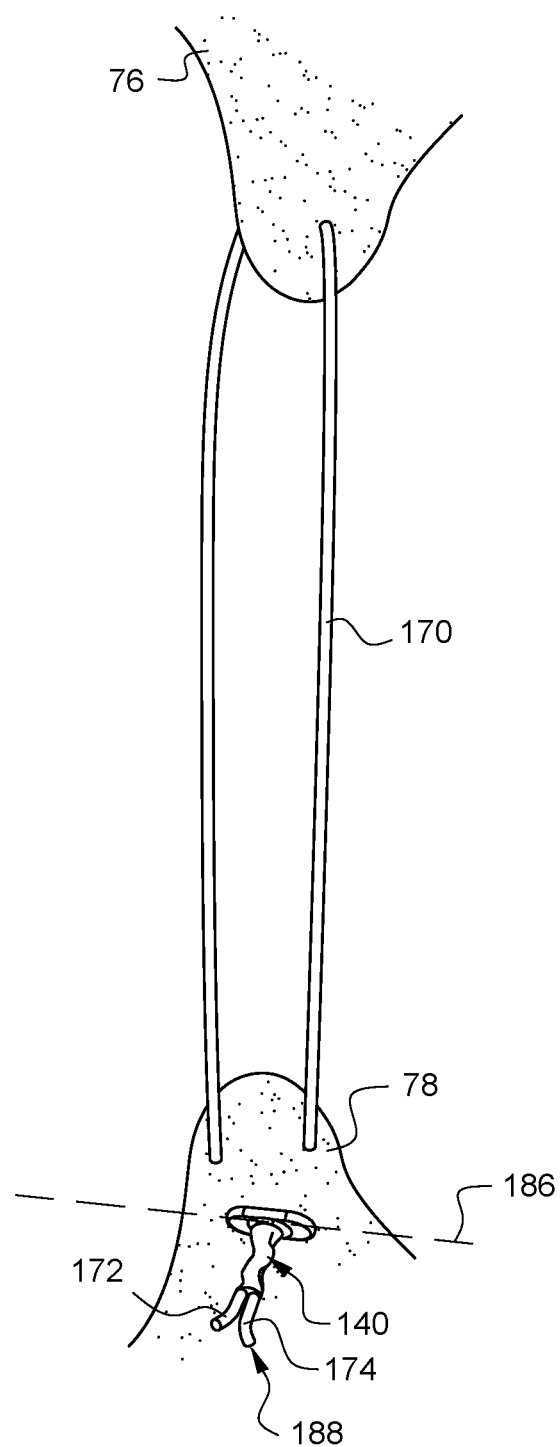

As shown in the enlarged view of FIG. 16C, the suture fastener applicator 158 is moved so that the entrance of the suture fastener 140 is placed against the papillary muscle 78, while the suture ends 172, 174 are tensioned 184 individually and/or separately to achieve a desired suture length between the mitral leaflet 76 and the papillary muscle 78. When the desired suture length is achieved, the suture fastener applicator 158 is activated, causing the suture fastener 140 to fasten onto the suture passing therethrough. In this example, the suture fastener applicator 158 crimps the suture fastener 140, the suture ends 172, 174 can be trimmed, and the suture fastener applicator 158 can be removed, resulting in the secured suture 170 illustrated in FIG. 16D. This secured single suture 170 acts as a replacement chordae tendinae as part of a mitral valve repair procedure. When secured as shown in FIG. 16D, the suture fastener 140 will tend to lie down by pivoting on an axis 186 substantially parallel to the longer dimension of the base. This pivoting action does not tend to occur as easily for suture fasteners with bases that are round. By positioning the suture fastener such that an axis 186 of the longer dimension is substantially perpendicular to a line drawn from the bottom 188 of the papillary muscle 78, the suture fastener 140 will tend to point down toward the bottom 188 of the muscle 78, thereby keeping it more out of the way of the heart's chamber and the structures therein. This may improve blood flow through the chamber while still allowing the chordae tendinae to be repaired.

Various advantages of an apparatus for mitral valve repair and methods thereof have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A surgical snare assembly, comprising:
   a suture fastener having a crimpable sleeve, an entrance, an exit, and a base perpendicular to the crimpable sleeve and adjacent to the entrance of the suture fastener, wherein the base has a face at the entrance, wherein the face is planar and has a length dimension and a width dimension perpendicular to the length dimension, and wherein the length dimension is greater than the width dimension;
   a suture passed through the suture fastener with an entrance suture portion coming out of the entrance of the suture fastener and an exit suture portion coming out of the exit of the suture fastener, the suture having a ferrule coupled to the exit suture portion;
   a suture engaging loop;
   a handle that extends from a first end to a second end, wherein the handle extends from the first end to the second end along a curved path, wherein the first end of the handle is coupled to the suture engaging loop, and wherein movement of the handle a first distance away from the suture fastener causes the suture engaging loop to move through the suture fastener from the entrance to the exit; and
   an applicator comprising a shaft extending from a proximal end to a distal end along an applicator axis, the shaft of the applicator comprising a suture fastener receiver disposed at a first location at the distal end of the shaft and a snare outlet disposed at a second location adjacent to the distal end of the shaft, the suture fastener receiver operable to removably maintain the suture fastener, a portion of the entrance suture portion, and a portion of the exit suture portion, wherein the entrance suture portion is disposed through the suture fastener receiver and the snare outlet, wherein the handle is operable to pass through the suture fastener receiver and the snare outlet, and wherein the suture fastener receiver extends from a first end to a second end along a receiver axis such that the suture fastener is configured to be inserted into the suture fastener receiver along the receiver axis, and the receiver axis is disposed along or parallel to the applicator axis.

2. The surgical snare assembly of claim 1, wherein:
   the exit of the suture fastener is inserted into the suture fastener receiver, while the entrance faces outward;
   the entrance suture portion and a portion of the handle protrude out of the snare outlet; and
   the exit suture portion protrudes out of the suture fastener receiver.

3. The surgical snare assembly of claim 1, wherein the snare outlet is an aperture formed at the second location adjacent to the distal end of the shaft of the applicator in a surface that extends parallel to the applicator axis.

4. The surgical snare assembly of claim 1, wherein the suture engaging loop and the handle are removably coupled to the applicator such that (a) the first end of the handle is disposed within a portion of the applicator adjacent to the distal end of the shaft of the applicator; (2) the second end of the handle is disposed outside of the applicator; and (c) a portion of the handle disposed between the first end and the second end is disposed within the snare outlet.

5. The surgical snare assembly of claim 1, wherein the curved path is a segment of a circular path.

* * * * *